US009452457B2

(12) United States Patent
Denvir et al.

(10) Patent No.: US 9,452,457 B2
(45) Date of Patent: Sep. 27, 2016

(54) COMPOSITION, SYSTEM, AND METHOD FOR TREATING WATER SYSTEMS

(71) Applicant: NCH Corporation, Irving, TX (US)

(72) Inventors: Adrian Denvir, Richardson, TX (US); David F Vela, Irving, TX (US); Christina B Burton, Irving, TX (US); Katrell D Copeland, McKinney, TX (US); Scott M Boyette, Irving, TX (US); Robert C Pearce, III, Arlington, TX (US)

(73) Assignee: NCH Corporation, Irving, TX (US)

( * ) Notice: Subject to any disclaimer, the term of this patent is extended or adjusted under 35 U.S.C. 154(b) by 616 days.

(21) Appl. No.: 13/745,211

(22) Filed: Jan. 18, 2013

(65) Prior Publication Data

US 2013/0239991 A1    Sep. 19, 2013

Related U.S. Application Data

(60) Provisional application No. 61/587,966, filed on Jan. 18, 2012.

(51) Int. Cl.
*B08B 7/04*     (2006.01)
*B08B 9/08*     (2006.01)
(Continued)

(52) U.S. Cl.
CPC ............. *B08B 9/0856* (2013.01); *A01N 37/16* (2013.01); *A01N 37/36* (2013.01); *C02F 1/50* (2013.01);
(Continued)

(58) Field of Classification Search
CPC .......... C02F 1/001; C02F 1/008; C02F 1/50; C02F 1/68; C02F 1/683; C02F 1/685; C02F 1/76; C02F 1/766; C02F 9/00; C02F 2101/30; C02F 2303/02; C02F 2303/04; C02F 2303/20; C02F 2303/22; C02F 2305/04; C02F 2305/14; B08B 3/04; C11D 1/38; C11D 3/33
See application file for complete search history.

(56) References Cited

U.S. PATENT DOCUMENTS

| 1,674,827 A | 6/1928 | Fleming |
| 3,106,541 A | 10/1963 | Lipowski et al. |

(Continued)

FOREIGN PATENT DOCUMENTS

| DE | 19859774 | 6/2000 |
| WO | WO2005021445 | 3/2005 |
| WO | WO2005051850 | 6/2005 |

OTHER PUBLICATIONS

Marigot Ltd. "GRAS Notification with respect to Phymatolithon calcareum and Lithothamnium corallioides" Jul. 1999.
(Continued)

*Primary Examiner* — Bibi Carrillo
(74) *Attorney, Agent, or Firm* — Ross Barnes LLP; Robin L Barnes; Monty L Ross

(57) ABSTRACT

A composition for treating a water system to remove scale, microorganisms and biofilm, and corrosion by-products. The composition comprises chelating agents and a surfactant. Depending on the water system being treated, the composition may be a solid dissolved by water in the system being treated or may be a pre-mixed foam or aerosol. A treatment system particularly suitable for flowing water systems comprises a container for holding such a treatment composition and mixing it with a portion of water from the water system, a filter for removing solids dislodged during treatment, and a corrosion monitor. A method for using such a treatment composition comprises draining substantially all existing water in the water system, filling or rinsing the system with fresh water, contacting the treatment composition with substantially all parts of the water system, and draining the treatment composition from the system before resuming normal operations.

33 Claims, 4 Drawing Sheets

(51) Int. Cl.
*A01N 37/16* (2006.01)
*A01N 37/36* (2006.01)
*C02F 1/50* (2006.01)
*C11D 11/00* (2006.01)
*C11D 1/29* (2006.01)
*C11D 1/62* (2006.01)
*C11D 1/72* (2006.01)
*C11D 3/20* (2006.01)
*C11D 3/48* (2006.01)
*C11D 17/00* (2006.01)
*C02F 1/00* (2006.01)
*C02F 1/68* (2006.01)
*C02F 1/76* (2006.01)
*B08B 9/00* (2006.01)
*C02F 9/00* (2006.01)
*C02F 101/30* (2006.01)
*B08B 3/04* (2006.01)
*C02F 103/02* (2006.01)

(52) U.S. Cl.
CPC ............ *C02F 1/683* (2013.01); *C11D 1/29* (2013.01); *C11D 1/62* (2013.01); *C11D 1/72* (2013.01); *C11D 3/2086* (2013.01); *C11D 3/48* (2013.01); *C11D 11/0023* (2013.01); *C11D 11/0041* (2013.01); *C11D 17/0043* (2013.01); *B08B 3/04* (2013.01); *B08B 9/00* (2013.01); *C02F 1/001* (2013.01); *C02F 1/008* (2013.01); *C02F 1/68* (2013.01); *C02F 1/685* (2013.01); *C02F 1/687* (2013.01); *C02F 1/76* (2013.01); *C02F 1/766* (2013.01); *C02F 9/00* (2013.01); *C02F 2101/30* (2013.01); *C02F 2103/023* (2013.01); *C02F 2303/02* (2013.01); *C02F 2303/04* (2013.01); *C02F 2303/08* (2013.01); *C02F 2303/20* (2013.01); *C02F 2303/22* (2013.01); *C02F 2305/04* (2013.01); *C02F 2307/08* (2013.01)

(56) References Cited

U.S. PATENT DOCUMENTS

| | | | |
|---|---|---|---|
| 3,173,864 A | | 3/1965 | Freedman |
| 3,410,649 A | | 11/1968 | Sellet |
| 3,428,557 A | * | 2/1969 | Rivers .................... 210/746 |
| 3,503,890 A | * | 3/1970 | Davisson et al. ......... 134/22.14 |
| 3,582,461 A | | 6/1971 | Lipowski et al. |
| 4,005,009 A | * | 1/1977 | Kinoshita et al. ............ 210/705 |
| 4,306,967 A | | 12/1981 | Trautwein |
| 4,383,077 A | | 5/1983 | Bankert |
| 4,830,761 A | | 5/1989 | Leach et al. |
| 4,931,187 A | | 6/1990 | Derham et al. |
| 5,057,229 A | * | 10/1991 | Schulenburg et al. ....... 210/743 |
| 5,253,759 A | | 10/1993 | Gouge et al. |
| 5,294,916 A | * | 3/1994 | Bolton et al. .............. 340/606 |
| 5,322,856 A | | 6/1994 | Martin |
| 5,576,481 A | | 11/1996 | Beardwood |
| 5,874,026 A | | 2/1999 | Pilsits, Jr. et al. |
| 6,040,406 A | | 3/2000 | Carrier et al. |
| 6,063,290 A | * | 5/2000 | Failon et al. ................. 210/699 |
| 6,149,821 A | * | 11/2000 | Rounds et al. ............... 210/754 |
| 6,149,822 A | | 11/2000 | Fabri et al. |
| 6,183,649 B1 | | 2/2001 | Fontana |
| 6,346,275 B1 | | 2/2002 | Auchincloss |
| 6,498,137 B1 | | 12/2002 | Schalitz et al. |
| 6,701,940 B2 | | 3/2004 | Tsibouklis et al. |
| 6,746,609 B2 | | 6/2004 | Stander |
| 6,797,197 B2 | | 9/2004 | Steimel et al. |
| 6,840,251 B2 | | 1/2005 | Gill et al. |
| 7,141,174 B2 | | 11/2006 | Steimel et al. |
| 7,537,705 B2 | | 5/2009 | Mizuno et al. |
| 7,632,412 B2 | | 12/2009 | Johnson et al. |
| 7,959,943 B2 | | 6/2011 | Hissong et al. |
| 7,976,873 B2 | | 7/2011 | Myntti et al. |
| 7,993,675 B2 | | 8/2011 | Oliver et al. |
| 2002/0185419 A1 | | 12/2002 | Chandler |
| 2003/0094406 A1 | | 5/2003 | Smith |
| 2003/0105072 A1 | * | 6/2003 | Degenhardt ............ A01N 43/36 514/210.17 |
| 2003/0108705 A1 | | 6/2003 | Duffield et al. |
| 2003/0200997 A1 | | 10/2003 | Gill et al. |
| 2005/0013878 A1 | | 1/2005 | Mingzhong et al. |
| 2005/0040363 A1 | * | 2/2005 | Gray ............................ 252/180 |
| 2007/0264296 A1 | * | 11/2007 | Myntti ................... A01N 25/30 424/405 |
| 2008/0017337 A1 | | 1/2008 | Duggirala et al. |
| 2008/0035580 A1 | | 2/2008 | de Rijk |
| 2008/0169239 A1 | * | 7/2008 | Sparks et al. ................ 210/631 |
| 2009/0258086 A1 | | 10/2009 | Myntti |
| 2010/0086576 A1 | | 4/2010 | Myntti |
| 2010/0261631 A1 | * | 10/2010 | Isobe .................... A01N 37/44 510/161 |
| 2011/0008220 A1 | | 1/2011 | Fleming et al. |
| 2011/0081713 A1 | | 4/2011 | Fleming et al. |
| 2011/0217761 A1 | | 9/2011 | Hilgren et al. |
| 2011/0293481 A1 | | 12/2011 | Eanes et al. |
| 2012/0067793 A1 | | 3/2012 | Ferrari et al. |
| 2012/0258156 A1 | | 10/2012 | Rumberger et al. |
| 2013/0099158 A1 | | 4/2013 | Moore et al. |
| 2013/0239991 A1 | * | 9/2013 | Denvir et al. ................... 134/10 |
| 2015/0125544 A1 | * | 5/2015 | Henderson et al. .......... 424/606 |
| 2015/0126425 A1 | * | 5/2015 | Henderson et al. .......... 510/247 |

OTHER PUBLICATIONS

M.A. Patrauchan et al., Calcium influences cellular and extracellular product formation during biofilm-associated growth of a marine *Pseudoalteromonas* sp., Journal 2005, 13 pg.

* cited by examiner

COMPOSITION, SYSTEM, AND METHOD FOR TREATING WATER SYSTEMS

CROSS-REFERENCE TO RELATED APPLICATION

This application claims the benefit of U.S. provisional patent application No. 61/587,966 filed Jan. 18, 2012.

BACKGROUND OF THE INVENTION

1. Field of the Invention

This invention relates to a treatment composition, system, and method for treating water systems for scale, biofilm and microbial growth, and corrosion. This invention is particularly useful in anthropogenic cooling and chilled water applications, such as cooling towers, and in drain systems, such as floor drains, hospital drains and waterless urinals.

2. Description of Related Art

Anthropogenic water systems are critical components commonly found in most of the world's energy producing facilities, industrial and manufacturing plants, hospitals, and other institutional complexes and buildings. These systems consume around 700 billion gallons of water annually with a cost of $1.8 billion in sewage handling costs alone. All of these anthropogenic water systems require some form of treatment, either chemical or non-chemical, to control the build-up of scale, biofilm and other corrosion by-products on the important heat transfer surfaces that are necessary for efficient system operation.

For water systems involving heat exchange, such as cooling towers, effective treatment to remove these contaminants and to prolong the amount of time before the systems are re-contaminated can safe significant amounts of money. An effective and thorough treatment may save costs for labor and treatment chemicals by reducing the frequency of periodic treatments or reducing the amount of chemicals needed for routine maintenance and/or periodic treatments. Such a treatment may also save on energy costs through the operation of clean heat exchange surfaces. Fouling of heat exchange surfaces costs U.S. industry hundreds of millions of dollars every year and is directly related to an increase in energy consumption of almost 3 quadrillion Btus (quads) annually.

To maximize the water usage and minimize waste, many of these systems employ a series of chemical treatments that protect the system against scaling, biofilm formation, and corrosion. For example the Chem-Aqua 15000 MTP product is one of the most common cooling tower chemical treatments, containing 2-phosphonobutane-1,2,4-tricarboxylic acid, and a series of high performance polymers to prevent calcium carbonate scale formation, azoles to inhibit copper corrosion and small amounts of molybdate for trace analysis. Chemical treatments such as the Chem-Aqua 15000 MTP product may be used with a number of non-oxidizing biocides including Bacticide 45 which is a 45% gluteraldehyde solution, Coolicide which is a 15% poly-quaternary ammonium solution, or a 1.5% Isothiazolin solution. In the larger industrial cooling tower systems and the cooling towers for coal and nuclear facilities it is more common to use sodium hypochlorite, 40% sodium bromide, or 11% bromine chloride liquid as the disinfectants.

These chemical treatments allow the water to be reused and recycled a number of times before it becomes necessary to discharge the water and replace it with fresh water. Increasing the duration for which the water may be circulated significantly reduces the amount of water that is discharged to the sewage system and minimizes the amount of make-up water that is needed to replace the bleed off. The chemical treatments also maintain the efficiency of the cooling tower and heat exchanger system. Many prior art treatment compositions and methods involve the use of liquid chemicals, typically shipped in large drums, which may make shipping and handling of the chemical compositions more difficult and expensive. Additionally, many prior art treatment compositions and methods may damage the components of the water system being treated as the chemicals used are highly corrosive. There is also an environmental down side to the treatments. It is estimated that there are 536 billion pounds of water treatment chemicals discharged as a result of cooling tower treatments every year, which may impact a variety of species living in or near areas and water-ways receiving the discharge. Therefore it is desirable to use treatment chemicals that are considered less toxic. For example, citric acid and sodium citrate, which are both approved food additives, have been used in treatment compositions.

Many prior art treatment compositions and methods are also effective at removing biofilms or require the use of strongly acidic, oxidizing, and toxic biocides for removal. Biofilms contain mixed communities of bacteria including various species embedded in an exopolymer or "slime layer". As bacteria begin to attach to a surface, they secrete polymers, such as polysaccharides and glycoproteins called fibronectin. These allow the bacteria to adhere to a surface and form the conditioning layer of the biofilm. Once a confluent surface of sessile cells has formed, any other bacteria that contact this layer will be captured. Thus bound in this way, these bacterial cells begin to produce anchoring organelles and other compounds, allowing a secondary layer to form on top of the conditioning layer. As cells continue to attach and accumulate, underlying layers continue to reproduce and create a dense bacterial cluster. As these biofilm layers form they also accumulate other inorganic and organic debris that grow within the pipe restricting flow and causing blockages.

Similar issues, particularly with biofilms, are also encountered in drainage systems, such as hospital drains, industrial wastewater drains, and waterless urinals. During normal use, drains and drainage systems transport liquids such as water, urine, or processing fluids to treatment or discharge facilities. Even though some of these liquids are sterile when then enter the drain systems, it is virtually impossible to keep all fluids sterile when they enter the outside environment. As they flow through the drainage system they accumulate naturally occurring micro flora and other heterotrophic microorganisms that, over time, result in the formation of biofilms along the surfaces of the walls of the pipes. In hospitals, especially dialysis centers, this could present a direct risk of infection to patients. Biofilms may also grow rapidly and result in clogged drains and piping in drainage systems.

Products and services for the cleaning and remediation of drains and drainage systems worldwide is estimated to exceed $2 billion annually, most of which is driven by labor costs that consume $0.87 for every dollar spent. As with the chemicals used to clean cooling tower and similar industrial water systems, the prior art drain remediation and cleaning technologies use aggressive chemicals, including concentrated acidic or basic compounds. These compounds need special handling and have to be stored on site or require specialty power cleaners such as water jets or drum and sectional machines that require experienced operators. They also typically involve added costs for protective gear for operators handling the chemicals and added training cots.

Many of the chemical drain cleaning products are sold in solid or liquid forms and are classified as alkaline drain openers, acid drain openers, or enzymatic drain cleaners. Alkaline drain openers come as either a solid or liquid and typically contain sodium or potassium hydroxide as well as sodium hypochlorite. In some cases the alkaline drain openers are sold as two part mixtures that will form a foam when mixed together in the drain. Alkaline drain openers can dissolve proteins and fats within the drain through an alkaline hydrolysis of the amide or ester. Acid drain openers usually contain a strong acid such as sulfuric acid that dissolves fats and proteins via an acid hydrolysis mechanism. They also have dehydrating properties that help them dissolve paper. Unlike the alkaline drain openers, most of these acid cleaners must be applied by a licensed operator. Enzymatic drain cleaners use bacterial cultures and concentrated enzymes that react with organic residues on the walls of the pipes, dissolving it to keep the drain flowing. These drain cleaners are intended to be used as a general maintenance treatments and not to remove clogs or blockages that have already formed. Mechanical drain cleaners are also known in the prior art and involve a number of mechanical and physical techniques to unclog and clean drain systems, which may be used alone or in combination with chemical cleaners. These mechanical cleaners include auger systems, air burst systems, plumber snakes, and water jet systems. These mechanical systems are advantageous because they do not have the hazards associated with the storage and use of harsh chemicals and they are relatively inexpensive and readily available for rent in most hardware stores. However, the disadvantage is that the mechanical removal of clogs and other biological deposits with these methods can be expelled into the environment putting the operator and other people in the vicinity at risk of exposure to biological pathogens. This is of particular concern in hospitals and dialysis centers where immunocompromised patients are being treated.

SUMMARY OF THE INVENTION

This invention relates to a chemical treatment composition, system and method for treating water systems, such as anthropogenic cooling and chilled water systems and drain systems, including dialysis and x-ray drains, urinals in port-o-potties, p-trap, and waterless urinals. Generally, these water systems are either "flowing" (or circulating or otherwise involving moving fluids) or "non-flowing" systems (or non-circulating systems) based on whether water is flowing through the system at the time of treatment. For example, a cooling tower would typically be a flowing system because water circulates through the system during treatment, whereas a drain would typically be a non-flowing system because water is not running through the drain during treatment. There are preferred embodiments for both types of water systems described herein; however, with modifications understood by those of ordinary skill in the art a water system may be switched from a flowing system to a non-flowing system, as desired, and a preferred embodiment for one type of system may be adapted for application to a water system that is typically considered to be the other type of system (for example, application of a non-flowing embodiment to a cooling tower) within the scope of the invention.

According to a preferred embodiment for a flowing water system, the treatment system comprises a side stream and a treatment product feeder containing a solid treatment product, preferably a product according to the treatment composition of the invention. A portion of the water from the system being treated is diverted to the side stream, where it contacts and dissolves the solid treatment product in the product feeder. The side stream, with the dissolved treatment product, is then reintroduced into the water system for further dilution and circulation throughout the system. The water containing the dissolved treatment product is then circulated throughout the water system for an effective period of time. The treatment system preferably includes a corrosion rack/corrosion monitor and a conductivity meter to monitor the effectiveness of the treatment product and the level of corrosion caused by the treatment product on the components of the water system being treated. According to another preferred embodiment, the treatment system comprises an in-line filtration mechanism to filter out biofilm agglomerates dislodged by the treatment composition.

A treatment composition according to one preferred embodiment of the invention, applicable to both flowing and non-flowing water systems, comprises chemical chelating agents (organic or inorganic acids and their corresponding neutral salts for metal ion sequestration from biofilm, hard scale, and bulk water) and a surfactant. Citric acid and sodium citrate are preferred chelating agents and tetradecyltrimethyl ammonium bromide is a preferred surfactant. When added to the water of the flowing water system being treated or with a given volume of water in a preferably pre-mixed, ready-to-use liquid or foaming formulation for treatment of non-flowing water systems, these reagents are preferably in concentrations of at least 0.001 M neutral salt, 0.0005 M acid salt. 0.00015 M surfactant, but not greater than 0.01 M neutral salt, 0.005 M acid salt and 0.0015 M surfactant. One or more corrosion inhibitors, particularly copper inhibitors such as tolyltriazole ("TTA"), are also preferably used with the reagents in the treatment composition in concentrations according to label specifications, typically between 2 ppm-17 ppm. A secondary biocide and/or anti-foaming agents are also preferably added to or used with the treatment composition for controlling microorganisms and water parasites and foaming.

In order to achieve the minimum concentrations of treatment composition described above to treat a small volume water system, it would be necessary to ship large volumes of liquid-based chemicals even when the volume of the water system being treated is relatively small. Shipping and handling such large volumes of liquid chemicals is costly and can be hazardous to personnel involved in the cleaning process. It is possible to produce and ship smaller volumes of concentrated liquid chemicals to use as the treatment composition. Using certain chelating agents and certain surfactants, such as tetradecyltrimethyl ammonium bromide and didecyldimethyl ammonium chloride, a 70× concentrated liquid formula is possible. However, use of a concentrated liquid formula limits the type of surfactant that can be used, because certain surfactants, such as SugaQuats, will precipitate from solution rendering the mixture inactive. Additionally, shipping and handling concentrated liquid treatment compositions can still be more costly and hazardous that if the treatment composition were in a solid form. Preferably, at least one component of the treatment composition is in a solid form that uses the water in the system being treated to dissolve and dilute the composition.

Drain systems typically require smaller amounts of treatment chemicals. Although handling such chemicals may still be hazardous, the issues related to shipping large quantities of the chemicals are not typically encountered. Additionally, unlike other circulating water systems, it may be more difficult for the treatment composition to contact all contaminated surfaces in a drainage system. A spray, flooded aerosolized or foaming formulation for the treatment composition is preferably used for drainage systems to aid in having the treatment reach all surfaces of the drain.

A method for treating water systems according to a preferred embodiment of the invention for a flowing water system comprises the steps of (1) bleeding or draining the water system and re-filling, as necessary, to remove the existing water and any previous water treatment compositions that may react with or otherwise interfere with the treatment composition; (2) determining the total volume of water in the system and re-filling the system with water; (3) adding a treatment composition so that the final concentrations of active reagents in the water system are greater than 0.001 M neutral salt, 0.0005 M acid salt, 0.00015 M surfactant; (4) optionally adding corrosion inhibitors (typically 2 ppm minimum), anti-foaming agents, and/or a secondary biocide, as desired; (5) circulating the water with the treatment composition throughout the system for a sufficient time; (6) periodically testing the system for corrosion products to monitor the corrosive effects of the treatment composition on the water system; (7) filtering the water to remove dislodged solids and biofilm agglomerates and monitoring the filter for necessary replacement; and (8) bleeding or draining the water containing the treatment composition from the water system after sufficient treatment time and removing any remaining solids in the sump or other water reservoir or low flow areas of the system, then refilling with fresh water. A method for treating water systems according to a preferred embodiment of the invention for a periodic or non-circulating flowing water system comprises the steps of: (1) optionally flushing the water system with fresh water; (2) optionally preparing a liquid, aerosol, or foaming treatment composition at the treatment site so that the final concentrations of active reagents in the water system are greater than 0.001 M neutral salt, 0.0005 M acid salt, 0.00015 M surfactant based on the volume of water used to prepare the treatment (alternatively, the treatment composition may be shipped as a pre-mixed or ready-to-use formulation); (3) applying the treatment composition to the water system by pouring, spraying, or foaming; (4) optionally adding corrosion inhibitors (typically 2 ppm minimum) and/or a secondary biocide, as desired; (5) re-applying the treatment composition to the water system as needed so that the total contact time of the treatment composition with substantially all contaminated surfaces in the water system is sufficient; (6) optionally testing the system periodically for corrosion products to monitor the corrosive effects of the treatment composition on the water system; and (7) optionally flushing the water system with fresh water.

As used herein, "fresh" water includes any source of water that is supplied to the water system from an available water source, such as a municipal water supply, a well, river, pond, or lake, or water recycled from another industrial process. Most typically, this water is from a municipal water supply. These methods result in a thorough cleaning of the water system, after which other, conventional water treatment regimens may be resumed and these methods utilized for periodic maintenance. Most preferably, the concentrations of active reagents of the treatment composition used with these preferred methods (when mixed with the water of the system for a flowing water system or when mixed with a given volume of water from an external source for a non-flowing water system) are 0.005 M neutral salt, 0.003 M acid salt, 0.00075 M surfactant. It is also preferred that the concentrations do not exceed 0.01 M neutral salt, 0.005 M acid salt, and 0.0015 M surfactant, as higher concentrations may result in excessive corrosion in water systems having copper, mild steel and galvanized steel components. It is also preferred to add commercially available corrosion inhibitors (particularly copper inhibitors if the water system has copper components), anti-foaming agents (or foam thickeners, when a foam is desired for application in non-flowing water systems), and biocides in amounts indicated on the product labels, along with the treatment composition.

One advantage of composition and methods of the invention is that it effectively removes biofilm and scale that are not effectively removed by conventional prior art treatment protocols. The treatment composition improves overall treatment performance as a result of a synergistic interaction between the reagents of the composition. The treatment composition, preferably having reagents in solid form that are dissolved on site using the water in the system being treated, also decreases the costs and risks associated with shipping and handling large volumes of liquid treatment chemicals. Additionally, the methods of the invention provides optimal cleaning while minimizing damage to the materials that make up the water system being treated.

BRIEF DESCRIPTION OF THE DRAWINGS

The system and method of the invention are further described and explained in relation to the following drawings wherein.

DESCRIPTION OF THE PREFERRED EMBODIMENTS

Figure 1:
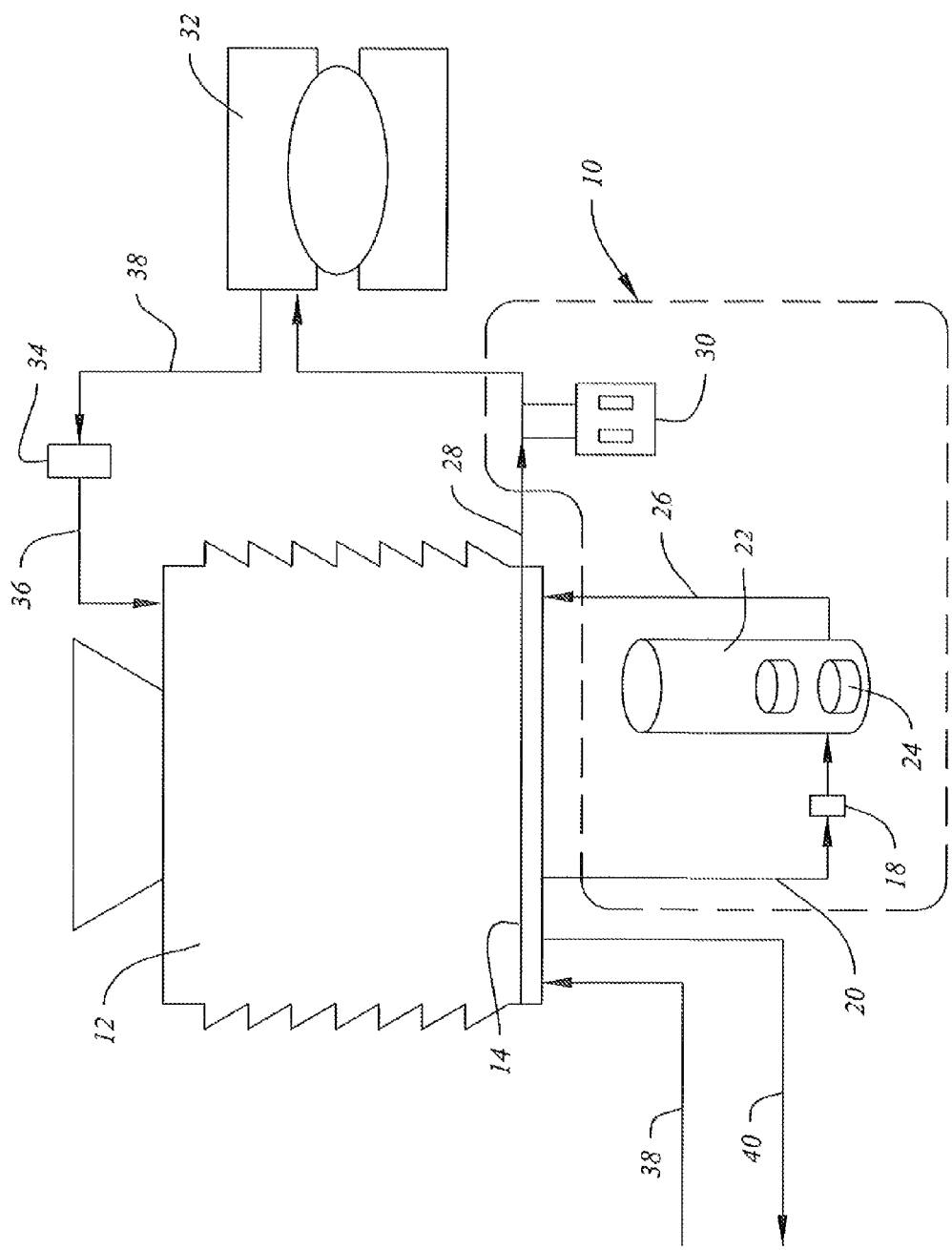
FIG. 1 is a side elevation view of one embodiment of a water treatment system according to the invention used with a flowing water system

Referring to FIG. 1, one embodiment of a system 10 for treating a typically flowing water system, such as a cooling tower 12, according to a preferred embodiment of the invention is depicted. It should be noted that FIG. 1 is not to-scale, but the components of system 10 and the water system are depicted in a manner that allows them to be viewed on a single page. In normal operation mode of the cooling tower 12, water is circulated from the tower sump 14 through the condenser 32 then back into the top of the cooling tower 12. Water may be drained or bled from cooling tower 12 through drain line 40 and fresh water added through supply line 38, as needed. The system 10 preferably comprises a side stream 20 that diverts water from the sump 14 to a product feeder 22 or container that houses a solid chemical treatment product 24. The treatment product 24 may be in solid block form or may be in powdered form, and is most preferably the treatment composition of the invention, although other treatment products or chemicals may be used with system 10, including liquid chemicals. Alternatively, a source of fresh water (other than water from the water system) may be used to initially dissolve the treatment product prior to adding to the volume of water in the water system, but it is preferred to use water from the system itself. Water preferably passes through filter 18 prior to entering product feeder 22, but filter 18 may be located in another area of the overall process loop. Filter 18 is preferably used to remove biofilm agglomerates and other solids dislodged from the surfaces of the water system by the treatment composition. Any suitable filter mechanism or material may be used that will remove solids dislodged from the water system and prevent them from being re-deposited or colonizing or contaminating other areas of the water system. Most preferably, system 10 also includes a pressure monitor to measure the pressure differential across filter 18. The pressure differential aids in monitoring filter 18 to determine when the filter is fouled and needs to be replaced, which may be required one or more times during a treatment cycle.

During a treatment cycle, water from sump 14 contacts treatment product 24 inside product feeder 22. Any configuration may be used for product feeder 22 that permits water from the system being treated to contact and dissolve the treatment product; however, a feeder similar to that described in published U.S. patent application Ser. No. 12/787,025 is preferred. For smaller scale water systems, including drain systems, a timed-dosage feeder, similar to that described in published U.S. patent application Ser. Nos. 12/498,793 and 12/571,714 may also be used with modifications that will be apparent to those of ordinary skill in the art. Product feeder 22 is preferably used as both a container for holding the treatment product prior to a treatment cycle and a reservoir for mixing the treatment product with at least a portion of the water from the water system to form a slurry that is then mixed with the rest of the water from the water system. Alternatively, product feeder 22 may contain the treatment product and deliver it to a pipe or separate reservoir for mixing with the water or a portion of the water from the water system.

Once the water has contacted the treatment product 24, it begins to dissolve in the water and is carried out of the product feeder 22 through discharge line 26. Discharge line 26 then delivers the water with dissolved treatment product back into sump 14 where it is mixed with a larger quantity of water and the treatment product is further diluted. Water containing the treatment product is discharged from sump 14 through process stream 28, which preferably passes through a corrosion rack/corrosion monitor 30, where the level of corrosion in the water system may be monitored, then through evaporator/chiller/condenser 32, and finally through conductivity meter 34 before feeding the top of cooling tower 12. It is preferred that an electrochemical corrosion monitor to measure real time corrosion in the water system during treatment and/or a corrosion rack containing coupons of the reactive metals in the water system to monitor the corrosion rates be used as part of corrosion rack/corrosion monitor 30. Conductivity meter 34 may already be in place as part of the water system to monitor conductivity during normal operational cycling of water through the system. These monitors are common in cooling towers, such as cooling tower 12, and are frequently tied to automatic bleeding systems that bleed water from the system when needed. If not already part of the water system, conductivity meter 34 is preferably included as part of treatment system 10 and located near corrosion rack/corrosion monitor 30, although both the conductivity meter 34 and corrosion rack/corrosion monitor 30 may be placed at other locations within the overall water system. The water with dissolved treatment product then circulates through the cooling tower 12, back to sump 14, where a portion is again diverted through stream 20 to contact treatment product 24 in product feeder 22. The process is repeated until all of the desired treatment product is dissolved and circulated through the water system for sufficient time to contact substantially all the components of the water system, such as piping, fill material, and sump walls, remove scale build-up, biofilm and microbiological growth, and other corrosion by-products.

Alternatively, the treatment product 24 may be added directly to the sump 14 (or other water reservoir of the water system to be treated), rather than using side stream 20 and product feeder 22. In this embodiment, the treatment product is held in one or more containers, such as a drum or small tank, prior to the treatment cycle. If ingredients for the treatment product are held in more than one container, they may be mixed together prior to the treatment cycle, if desired. The treatment product is then mixed with at least a portion of the water from the system, or with another source of fresh water if desired, in one or more reservoirs, with the resulting mixture or slurry then being added to the water system to mix with the volume of water in the system. The reservoirs for mixing the treatment product with water may be the same as the containers for holding the treatment product or they may be separate. The reservoir may also be part of the water system itself, such as the sump of a cooling tower.

Regardless of how the treatment product is added to the water system, it is preferred that it be added so that the concentration of active agents in the total volume of water in the system is at least 0.001 M neutral salt, 0.0005 M acid salt, 0.00015 M surfactant, but not greater than 0.01 M neutral salt, 0.005 M acid salt, and 0.0015 M surfactant. Most preferably, the concentrations in the treated water are around 0.005 M neutral salt, 0.003 M acid salt, 0.00075 M surfactant. A corrosion inhibitor is also preferably used with the treatment product in a minimum amount of 2 ppm, and most preferably around 17 ppm. Other treating agents, such as a secondary biocide and anti-foaming agents, may also be added to the water system, either through side stream 20 or directly into sump 14 or other water reservoir in the existing water system, if they are not already included as part of the treatment product.

System 10 may also include other components, such as pumps, valves, and flow meters, which will be understood by those of ordinary skill in the art. System 10 may be permanently installed at a treatment site or may be portable and transported to a water system needing treatment as needed. If portable, treatment system 10 preferably includes quick connection ports for connecting system 10 to the process flow lines or water reservoir of the water system being treated. Similar connection ports may be permanently installed as part of the water system, if not already present, to allow easy periodic treatment of the water system using treatment system 10.

A treatment system similar to system 10 may also be used with non-flowing or non-circulating water systems, such as a drain or a tank. Preferably, the water system is capable of holding a volume of water for a period of time so that the treatment product may contact substantially all the contaminated components of the water system for effective treatment. With a drainage system, the piping may include valves that may be shut-off to stop the flow of water out of the drain, a clog may shut-off the flow of water, or an inflatable bladder may be inserted into the drain or pipe and expanded to shut-off the flow of water, all allowing the drainage system to temporarily hold a volume of water into which the treatment product may be added to be dissolved and diluted. An automated product feeder may be used to dispense treatment product into the non-circulating water system. Alternatively, a simple container may be used to hold the treatment product and used as a reservoir for pre-mixing the treatment product with water to dilute and dissolve it prior to introducing it into the water system. The treatment system may further include a mixer for agitating the water containing the treatment product within the water system to aid in contacting the treatment product with all components of the water system, if the water system does not already have such a mixer. In another embodiment, the treatment system may include piping and a pump to create a temporary circulating system during a treatment cycle.

A treatment composition according to one preferred embodiment, particularly suitable for use in circulating water systems (such as cooling tower) and larger scale non-circulating systems (such as large tanks), comprises chemical chelating agents (organic or inorganic acids and their corresponding neutral salts) and a surfactant. Most preferably, the acid is citric acid and the salt is sodium citrate. These chelating agents aid in metal ion sequestration from any biofilm, hard scale, and bulk water present in the water system being treated. The surfactant is preferably a cationic surfactant, and most preferably a surfactant with antimicrobial properties. Preferred surfactants include ammonium bromide compounds, ammonium chloride compounds, alcohol ethoxylates, and alcohol ethoxysulfates (AES). The surfactant aids in swelling and dissolving the extra cellular polysaccharide matrix that makes up a biofilm. In addition it can create an antimicrobial environment for microorganisms or water borne parasites that may be present in the water or biofilm environment. One or more commercially available corrosion inhibitors are also preferably included in the composition or separately added to the water system during a treatment cycle to protect the metallic components of the water system being treated.

A secondary biocide and an anti-foaming agent may also be used as part of the composition or separately added to the water system during a treatment cycle, and are preferably used, to provide an antimicrobial environment in the bulk water to prevent secondary contamination of the water source as biofilm agglomerates are sloughed off the primary biofilm surface being treated and to control foaming. These commercially available components are added according to product label specifications.

For the treatment to be effective it is preferred that the aqueous treatment solution, (i.e. treatment composition with the total water volume of the system being treated), have the following minimum concentrations: 0.001 M in the neutral salt, 0.0005 M in the acid salt, 0.00015 M in the surfactant, but concentrations not greater than 0.01 M neutral salt, 0.005 M acid salt, and 0.0015 M surfactant. The corrosion inhibitor(s) are used at the specified labeled usage rates, but preferably at least 2 ppm of corrosion inhibitors are used in or with the treatment composition. Additional corrosion inhibitors may be added if corrosion rates in the system are observed to increase during the treatment, which may vary according to the concentrations of the other components of the treatment composition and the duration of the treatment cycle. Most preferably, the concentrations in the treated water are around 0.005 M neutral salt, 0.003 M acid salt, 0.00075 M surfactant, and 17 ppm corrosion inhibitor.

In order to achieve the minimum concentrations of treatment composition described, and to allow the use of a wider variety of surfactants without the problems associated with the surfactant precipitating out of solution when the treatment composition is shipped as a concentrated liquid formula, it is preferred that at least one component of the treatment composition be in a solid form. Most preferably, all of the components of the treatment composition (and any other additives, such as corrosion inhibitors, secondary biocides, and anti-foaming agents) are in a solid block or powdered form that are dissolved and diluted by the water contained in the system being treated.

A treatment composition according to another preferred embodiment, particularly for use in non-flowing water systems, such as drainage systems, comprises the same chemical chelating agents (organic or inorganic acids and their corresponding neutral salts, preferably citric acid and sodium citrate) and a surfactant as previously described. These chemicals may be shipped to a treatment site in solid form, preferably as powders, for mixing with water at the site or may be shipped as a pre-mixed or ready-to-use liquid or foaming formulation. For the treatment to be effective, it is preferred that an aqueous treatment solution, (i.e. treatment composition with the total volume of water added or the total volume of water held in the drainage system if the flow of water is capable of being shut-off to contain a volume of water), have the following minimum concentrations: 0.001 M in the neutral salt, 0.0005 M in the acid salt, 0.00015 M in the surfactant, but concentrations not greater than 0.01 M neutral salt, 0.005 M acid salt, and 0.0015 M surfactant. In order to ensure the treatment composition reaches all contaminated surfaces, it is most preferably applied as an aerosol or a foaming formulation. A corrosion inhibitor, a foam thickener (as opposed to an anti-foaming agent for use in water systems such as cooling towers), and a propellant are preferably added to the treatment composition. Any compatible aerosol propellant may be used, although AB-46 is the preferred propellant. A secondary biocide may also be used.

The treatment composition will contain the chelating agents and surfactant in proper weight percentages to allow specified quantities to be added to a given volume of water to achieve the above concentration ranges. The chelating agents and surfactant may be pre-mixed in a solid block form or a mixed powder or a slurry prior to addition to the water system, or they may be separately added as either solid, liquid, or slurry components, depending on the type of water system being treated. Preferably, at least one of these components of the treatment composition is in a solid block or powdered form and most preferably, particularly for flowing water systems, the chelating agents and surfactant are pre-mixed into a solid block or a powdered mixture, where the solids are dissolved by the water in the system being treated. However, it may be beneficial to allow the surfactant to circulate through the water system (or otherwise contact the components of the water system) for a period of time to begin breaking down biofilms in the system prior to adding the chelating agents, so separate components may also be used. One or more corrosion inhibitors and a secondary biocide are preferably added to the water system being treated and anti-foaming agents or foam thickeners and a propellant, depending on the application, may also be added as needed. These additives may be in solid or liquid form, may be incorporated as part of a pre-mixed solid block or powdered mixture or pre-mixed or ready-to-use liquid, aerosol or foaming formulation along with the chelating agents and/or surfactant, or may be separately added at the treatment site as solids, liquids, slurries, or mixtures thereof.

A preferred method for treating a flowing water system according to the invention comprises the following steps: (1) bleeding or draining the water system to remove the existing water (if any) and any previous water treatment chemicals; (2) determining the total volume of water in the system (or the volume of water the system is capable of holding during normal operations for a circulating system or capable of holding to fill the system in a non-circulating system) and also re-filling the system with water; (3) adding a treatment composition so that the final concentrations of active reagents in the water system are greater than 0.001 M neutral salt, 0.0005 M acid salt, 0.00015 M surfactant; (4) optionally adding corrosion inhibitors (typically 2 ppm minimum), anti-foaming agents or foam thickeners (depending on the water system), and/or a secondary biocide, as desired; (5) circulating the water with the treatment composition throughout the system (or contacting the water with the treatment composition with substantially all components of a non-circulating system) for a sufficient time; (6) periodically testing the system for corrosion products to monitor the corrosive effects of the treatment composition on the water system; (7) in a circulating system, filtering the water to remove dislodged solids and biofilm agglomerates; and (8) bleeding or draining the water containing the treatment composition from the water system after sufficient treatment time and removing any remaining solids in the sump or other water reservoir or low flow areas of the system (if any), then refilling with fresh water as applicable. This preferred method may also be used with non-flowing water systems, where the water system is capable of holding a volume of water for a given time. For example, this method may be used with a drain in which an inflatable bladder is inserted as a stopper and the drain pipe filled with a volume of water to allow the treatment composition to contact substantially all contaminated parts of the drain (from near the floor or basin in which the drain is installed down to a point at or near where the pipe joins another pipe or a trap). In such an application, the corrosion testing step may not be necessary.

With non-flowing water systems that are not capable of holding a volume of water, such as certain drainage systems, a preferred method comprises the following steps: (1) optionally flushing the water system with fresh water; (2) optionally preparing a liquid, aerosol, or foaming treatment composition at the treatment site so that the final concentrations of active reagents in the water system are greater than 0.001 M neutral salt, 0.0005 M acid salt, 0.00015 M surfactant based on the volume of water used to prepare the treatment (alternatively, the treatment composition may be shipped as a pre-mixed formulation); (3) applying the treatment composition to the water system by pouring, spraying, or foaming so that it contacts substantially all contaminated surfaces of the water system (such as the portion of a drain from near the floor or basin in which it is installed down to a point at or near which it joins another pipe or a trap); (4) optionally adding corrosion inhibitors (typically 2 ppm minimum) and/or a secondary biocide, as desired; (5) re-applying the treatment composition to the water system as needed so that the total contact time of the treatment composition with substantially all contaminated surfaces in the water system is sufficient; (6) optionally testing the system periodically for corrosion products to monitor the corrosive effects of the treatment composition on the water system; and (7) optionally flushing the water system with fresh water.

These methods result in a thorough cleaning of the water system, after which other water treatment regimens may be resumed and these methods utilized for periodic maintenance. Most preferably, the final concentrations of active reagents of the treatment composition in the water system are 0.005 M neutral salt, 0.003 M acid salt, 0.00075 M surfactant. A corrosion inhibitor, preferably TTA, at a concentration of at least 2 ppm and preferably at 17 ppm is added to the water system being treated to protect its components (particularly any copper components) from corrosion by the treatment composition chemicals. It is also preferred that the final concentrations of these reagents in the water system do not exceed 0.01 M neutral salt, 0.005 M acid salt, and 0.0015 M surfactant, as higher concentrations may result in excessive corrosion in water systems having copper, mild steel, and galvanized steel components. Most preferably, the method of the invention for flowing water systems is used with the solid block or powdered treatment composition and with the treatment system of the invention. Most preferably, the method of the invention for non-flowing systems is used with a pre-mixed or ready-to-use liquid, aerosolized, or foaming formulation of the treatment composition of the invention.

Prior to beginning the treatment, the volume of water in the water system, such as the cooling tower 12 in FIG. 1, is determined. Based on this volume, the amount of treatment composition needed to give the correct concentrations of active components as described above is placed in a container or mixing vessel that is transported to the treatment site. In another embodiment for water systems not capable of holding a volume or water, the treatment composition is preferably pre-mixed or ready-to-use in the proper concentrations. Alternatively, the treatment composition may be mixed at the treatment site by using any appropriate volume of water from outside the non-flowing water system, with it being preferred to use smaller volumes of water to reduce the reagents needed to give the preferred concentrations as additional treatments may be applied as necessary. If the water in the system (if any) contains high levels of cationic species, there is the potential that the chelating agents will be consumed before they reach the reaction zone. Therefore to minimize parasitic reactions the system should be bled to a point where the conductivity of the water in the system is the same value as the water being used to make up water loss resulting from normal operation. Alternatively, and particularly for smaller scale systems, such as drains and small tanks, the system may be completely drained prior to introducing the treatment composition.

After any necessary bleeding or draining of the system and re-filling with an appropriate volume of water (if the water system is capable of holding a volume of water), the treatment composition may be added to the water in the system. With larger scale circulating water systems, such as cooling towers, water from the system is preferably diverted through a side stream to the feeder, container, or mixing vessel housing the treatment composition, such as the use of side stream 20 and product feeder 22 in FIG. 1. As the water flows through the container/mixing vessel, the solid components of the treatment composition are dissolved and re-introduced into the water system where the treatment composition mixes with additional water to form the active product. Although it is preferred to use a side stream, the treatment composition can be mixed directly into any water system vessel or process stream (such as sump 14 or discharge line 28 in FIG. 1).

With non-circulating systems, such as drains, or smaller scale circulating systems, the treatment composition is preferably added directly to the water system rather than using a side stream, although a side stream may be added to an existing drain system if desired. The method of application may vary depending on the type of system involved, whether the system is capable of holding a volume of water (such as a tank or through the use of shut-off valve to hold water in a pipe) and the volume of water that may be held. For example, in a drainage system, the drain pipe may hold an appropriate volume of water to allow direct application of a solid, preferably powdered, treatment composition. The use of an inflatable bladder, inserted to a particular depth within the drain pipe, or a shut-off valve (if available and accessible) may be used as the shut-off mechanism to hold the water during the treatment cycle. Alternatively, a liquid treatment composition may be used and sprayed, aerosolized, or foamed into the drain or other water system. When smaller volumes of treatment composition are needed, the treatment composition may be shipped to the treatment site as a pre-mixed liquid, aerosol or foaming formulation. Although a pre-mixed formula is preferred, the treatment composition may be mixed at the treatment site with a given volume of water from outside the water system to form a liquid, aerosol, or foaming formulation which is then poured, sprayed, or otherwise added to the water system. A sprayed liquid, foam or aerosol application is most preferred when the water system is not capable of holding a volume of water. When mixed with water from outside the water system, deionized water is preferably used. Different spray nozzles, such as a directional sprayer or a long spray tube that is insertable in the opening of a drain cover, may be used to aid directing the treatment composition to all surfaces within the water system to be treated. Application of the treatment composition in a foaming formula is preferred for drain systems because the foam will expand to contact substantially all surfaces of the drain and will remain in contact with those drain surfaces for a longer period of time than most liquid applications, allowing time for the treatment composition to work on removing biofilms and other contaminants. Preferably, the foaming treatment composition is foamed into the drain line until a solid column is achieved from the base of the drain to the top of the drain.

The concentrations of reagents for the treatment composition used for non-circulating water systems are the same as for circulating water systems. When mixed with a volume of water held in the water system or with a volume of water in an external container are preferably between 0.001 M-0.01 M neutral salt, 0.0005 M-0.005 M acid salt, and 0.00015 M-0.0015 M surfactant, with these concentrations being determined based on the quantities of these reagents and the water, prior to addition of any other additives, such as corrosion inhibitors.

For either circulating or non-circulating water systems, other additives, such as corrosion inhibitors, anti-foaming agents (or foam thickeners and a propellant), and a secondary biocide may optionally be added through the side stream, product feeder, directly into the water system, or through an external container or sprayer, if these additives are not already part of the solid, powdered or liquid chemical materials containing the chelating agents and surfactant. These other additives are preferably added according to the product label specifications for each, as commercially available products. The order of addition of these chemicals and additives is not critical, but it is preferred that the corrosion inhibitor be added before or at the same time as the chelating agents and surfactant.

As the water system circulates the treated water (or the treated water is held within a non-circulating system or contacts the components of a non-circulating system), the dissolved treatment composition begins to contact the contaminated surfaces. The chelating agents attack any biofilm present on the surfaces and remove the metal bridging links that hold the extracellular polysaccharide matrix together. The surfactant and water penetrate the biofilm swelling it which in turn enables penetration of the chelating reagents to further break apart the matrix. As the extra polysaccharide matrix swells it sloughs off the outer exposed layers which are now soluble. It also sloughs of larger biofilm agglomerates which enter the bulk water flowing through the system. As the water flows, these agglomerates are transported to other areas of the system where they can settle out (particularly in low flow areas, such as the sump) and become a secondary source of contamination. The container/mixing vessel, side stream, or other process stream may be fitted with a filter to remove these biofilm agglomerates before they have a chance to reestablish colonies in the clean parts of the system. The water containing the dissolved treatment composition continues circulating through the water system (or being held within a non-circulating system) for a period of time to achieve effective cleaning of the water system. The duration of a treatment cycle will depend on factors such as the concentration of the active components of the treatment composition in the water system, the specific surfactant used, the flow rate of water through the system (or any mixing in a non-circulating system), and the degree or level of materials that need to be cleaned from the system, as will be understood by those of ordinary skill in the art. With larger circulating systems, such as cooling towers, the treatment cycle is typically 24-48 hours. With smaller scale systems, such as drains, the treatment cycle may be 5 minutes to a few hours. With drainage systems that do not hold a volume of water, the treatment composition may not fully contact all contaminated surfaces during an initial application or may not contact those surfaces for a sufficient period of time before draining from the system. As such, it may be necessary to do multiple treatments to achieve contact with contaminated surfaces for a sufficient time.

Many of the anthropogenic water systems use materials that can react with the chelating agents, the surfactant, or even the secondary biocide. As such, the system may be monitored for the formation of corrosion and corrosion by-products during treatment. It is preferred that an electrochemical corrosion monitor be used to measure real time corrosion in the system during treatment. Additionally, a corrosion rack containing coupons of the reactive metals in the system may be placed in the product stream to monitor the corrosion rates. The presence of the corrosion inhibitors should prevent many of the critical components of the system from being attacked. The range of concentrations for the active components of the treatment composition according to the invention should have minimal corrosive impact on the water system when used with suitable corrosion inhibitors; however, concentrations of active components of the treatment composition that are above the upper limit of the range (more than 10× the minimum values of 0.001 M neutral salt, 0.0005 M acid salt, 0.00015 M surfactant) may result in unacceptably high corrosion rates for long term treatment. At such high concentrations, the corrosion rates on mild steel, galvanized steel, and copper after 24 hours of treatment may be up to an order of magnitude higher than the acceptable limits. Additionally, these higher concentrations in the presence of galvanized steel in high laminar flow environments have been shown to produce a waxy coating that comprised the surfactant and the chelating chemicals. However, when using the treatment composition according to the invention at the minimum concentration values it was found that the corrosion rates on mild steel were lower than that observed with the known treatment compositions.

Many flowing water treatment systems use increasing conductivity (resulting from increased metal ion and carbonate concentration as the water is cycled) as an indicator and trigger to bleed off water and add fresh water. This practice helps prevent and slow down the formation of hard scale in the system. When the treatment composition is fully added to the water system according to the invention, the conductivity of the water will typically increase by 800 µS or 900 µS. This increase is normally sufficient to trigger the water system to bleed water to the drain, which would result in wasting the treatment composition before it has sufficient time to circulate through the water system for an effective treatment period. Therefore prior to adding any treatment composition to the water system, it is preferred to disable the bleeding mechanism for the system to prevent pre-mature discharge of the treatment chemicals.

In certain cases where flow is restricted or there is significant agitation there is the potential for the surfactant in the system to generate foam. To prevent foaming, an anti-foaming agent is preferably added to the system along with the treatment composition (if not already included as part of that composition). Secondary biocides may also be added, if not already included.

During a treatment cycle, circulating or otherwise moving water is preferably filtered to remove solids that are dislodged by the treatment. The filter should be monitored and replaced when it becomes fouled. This will be indicated by a visible soiling of the filter or by measuring an increase in pressure across the filter material. This helps prevent the filter material from becoming a secondary source of contamination that could result in further colonization of clean parts of the system. It is preferred that upon completion of the cleaning process the filter be removed from the system.

Upon completion of a treatment cycle, the water (including any remaining dissolved treatment composition and reactive reagents that have been spent during the process) should be evacuated from the water system. This helps prevent the deactivated organic load from becoming a secondary food source for microorganisms that will ultimately colonize the water system between treatment cycles. It is preferred that when cleaning is complete all the water in the system is dumped to the waste drain or receptacle. This will allow any solids that have settled the low flow areas to be removed from the system. Alternatively, a bleed valve activated by the water conductivity can be activated if present as part of the existing water system. This will drain the treatment composition and spent reagents from the system, however; there is the potential for low level residual treatment composition to remain for several weeks after the treatment is complete. After the treatment time has elapsed, the stopper can be removed and the liquid can be allowed to drain into to the main line and out to the waste treatment. Once the treatment time has elapsed, the sides of the walls will be sprayed with water which helps force the foam and broken up biofilm agglomerates down into the main drain lines and out to the waste treatment.

Once drained or bled, the water system may be refilled with fresh water (as applicable for flowing water systems) and normal operations resumed. Other treatment compositions, such as biocides and corrosion inhibitors, may be used during normal operations; however, it is preferred to periodically repeat the treatment method of the invention to thoroughly clean the water system as it has been found that even water systems appearing to be clean contain microorganisms, algae, and biofilms that are removed by the treatment composition and method of the invention.

The treatment compositions and methods for using such compositions according to the invention are further described and explained in relation to the following experimental examples:

EXAMPLE 1

Treatment of Biofilm Contaminated Coupons in the Laboratory Setting

Biofilm coupons containing multiple bacterial species were produced using a semi-batch bioreactor system in a laboratory setting. The biofilm reactor was designed around a continuous stir tank reactor and was fabricated using a 5 liter PVC container and contained 4 coupon holders and a central drive paddle that was used to induce a controlled fluid flow around the suspended coupons. The drive paddle was made from a Perspex paddle (10 cm×5 cm) that was attached to a 19 cm PVC rod and screwed into the drive of a gear DC motor with a gear ratio of 1:10 (Tanner Electronics). The coupon holders were also fabricated from PVC rods (14 cm) that were fixed in place through the lid if the biofilm reactor. The coupon rods were tapered at the bottom to enable easy fastening of both glass slides and metal coupons. Prior to operation, the reaction chamber and the individual components were disassembled, soaked in a 5% bleach solution then scrubbed in hot soapy water and rinsed in distilled water. Once cleaned the stir tank reactor was charged with 2 liters of reactor DI water and 20 g of the Free-Flow pellets containing bacteria (available from NCH Corporation or its divisions) was added to the water. Coupons were placed onto the coupon holding rods which were inserted into the Free Flow pellet material. The motor was connected to a RSR DC Power Supply Model HY3010E and the current set to 5 Volts giving a linear velocity of 0.4 feet per second across the face of the coupons. The reactor was run for 6 days with the Free Flow solution being replaced every 2 days. Standard microbiological assays showed that the system generated uniform biofilms with microbial populations exceeding $10^8$ CFU per ml of recovered supernatant.

These biofilm containing coupons were exposed to the treatment composition of the invention for 24 hours at three different concentration levels as follows:

Lowest concentration—0.0001M neutral salt (sodium citrate), 0.00005 M acid salt (citric acid), and 0.000015 M surfactant (tetradecyltrimethyl ammonium bromide);

Minimum concentration—0.001 M neutral salt (sodium citrate), 0.0005 M acid salt (citric acid), and 0.00015 M surfactant (tetradecyltrimethyl ammonium bromide); and Maximum concentration—0.01 M neutral salt (sodium citrate), 0.005 M acid salt (citric acid), and 0.0015 M surfactant (tetradecyltrimethyl ammonium bromide).

After the treatment, the slides were removed and the biofilm was processed to enumerate viable bacteria existing in the biofilm and also viable microorganisms in the supernatant liquid collected after processing. The results show that at the lowest concentration (10× below the recommended minimum concentration) there was no observable reduction in microorganisms in the biofilm or in the water showing that the biofilm was still viable (and growing). In the minimum concentration treatment, there was a 1 log reduction in the biofilm and the biofilm supernatant In the maximum strength treatment there were no recoverable microorganisms on the coupons or in the supernatant. The results are summarized in Table 1.

TABLE 1

Recoverable microorganisms at different treatment composition concentrations

| Slide | CFU/ml Recovered from Biofilm |
|---|---|
| Control (initial reading) | $1.0 \times 10^6$ |
| Control (after 24 hours) | $1.3 \times 10^7$ |
| Lowest Concentration (initial reading) | $2.8 \times 10^6$ |
| Lowest Concentration (after 24 hours of treatment) | $3.8 \times 10^7$ |
| Minimum Concentration (initial reading) | $5.0 \times 10^5$ |
| Minimum Concentration (after 24 hours of treatment) | $9.4 \times 10^4$ |
| Maximum Concentration (initial reading) | Below detection limit |
| Maximum Concentration (after 24 hours of treatment) | Below detection limit |

EXAMPLE 1A

Example 1 was repeated again but in this case a commercially available secondary biocide, MB-2128, was added to aid the initial treatments. In this case it was observed that after processing the biofilm and supernatant at the lowest concentration treatment there was a 2 log reduction in the microorganism counts. For the minimum and maximum concentration levels there were no detectable microorganisms recovered from the biofilm or from the supernatant. The results are summarized in Table 2.

TABLE 2

Recoverable microorganisms at different treatment composition concentrations with a secondary biocide

| Slide | CFU/ml Recovered from Biofilm |
|---|---|
| Control (initial reading) | $1.0 \times 10^6$ |
| Control (after 24 hours) | $1.3 \times 10^7$ |
| Lowest Concentration (initial reading) | $8.5 \times 10^4$ |
| Lowest Concentration (after 24 hours of treatment) | $9.8 \times 10^5$ |
| Minimum Concentration (initial reading) | Below detection limit |
| Minimum Concentration (after 24 hours of treatment) | Below detection limit |
| Maximum Concentration (initial reading) | Below detection limit |
| Maximum Concentration (after 24 hours of treatment) | Below detection limit |

EXAMPLE 1B

The process of Example 1 was repeated with the use of a commercial dispersant on the MB-2128 present in the same concentrations as Example 1A, but without the treatment composition of the present invention. When the treated solution and biofilm were processed it was found that there was only a 3 log reduction in the biofilm and supernatant were achieved.

The results of Examples 1, 1A, and 1B show that using the maximum strength concentration of the reagents was highly effective at removing biofilm and eliminating microorganisms in the solution and in the biofilm. The minimum concentration showed some efficacy at removing biofilm and reducing microorganisms when used alone; however; when the treatment composition was used with a secondary biocide there was a marked improvement in performance with no viable bacteria being recovered in the sessile or planktonic states. In addition the performance of the minimum concentration solution when used with the secondary biocide out-performed the commercial bio-dispersant when used with the same biocide, as shown by a comparison of Example 1A and Example 1B.

EXAMPLE 2

Treatment of a Pilot Cooling Tower with the Minimum Concentration Reagents and the Secondary Biocide In order to test the laboratory results on a larger scale, a study was conducted with a pilot cooling tower. A total volume of 28 gallons and a flow rate of 4 gallons per minute was used as the test system. The cooling tower had not been operational for over 1 year and a substantial biofilm had established in the pipes and hoses in the system. The sump was filled with municipal water and the pumps activated to start the flow of water. After 2 hours of operation water samples from the sump were collected and analyzed for the presence of microorganisms. In addition swab samples of the internal surfaces were collected and processed for microbiological analysis. The results of the analysis showed that water had $4 \times 10^2$ CFU per ml planktonic bacteria and $1 \times 10^6$ sessile bacteria. The microorganism analysis also showed that the biofilm was a multispecies form with a wide variation that represents a true consortia that would be found in real world environments.

The system was treated with the a concentrated solution of the citric acid, sodium citrate, and tetradecyltrimethyl ammonium bromide composition so that when all the components were added, the water in the system had the minimum reagent concentration of 0.001M, sodium citrate, 0.0005 M citric acid, and 0.00015 M tetradecyltrimethyl ammonium bromide. A secondary biocide, MB-2128, was added to give a final concentration of 200 ppm. When the reagents were added there was some foam forming at the air/water interface in the sump and some foam was observed at other points in the system. Samples of the water were collected after 1 hour, 24 hours, and 4 days. The results showed there was a half log reduction in the planktonic bacteria after 1 hour which increased to a 1 log reduction after 4 days treatment. Swabs of the biofilm in the hose showed that there was a 5 log reduction during this 4 day treatment time.

Visual inspection of the sump and hose reveled that biofilm had sloughed from the hoses and other system components during the process and were deposited in the low lying areas of the sump and in the inline filters. When analyzed this sump residue was shown to have $1 \times 10^3$ CFU per ml when re-suspended in buffer.

Prior to treatment the biofilm was a dark brown slime layer adhered to the surface of the pipes and tubes. When exposed to the treatment, it was observed that the biofilm color lightened and swelled after 2 days and finally got even lighter in color and began to detach from the surface and fall off in agglomerates. The most likely mechanism for these observations is that the exterior surface of the biofilm is attacked by the chelating agents and the surfactant dissolving the bridging metals that fix the extra polysaccharide polymers releasing them into solution and allowing the surfactant and water to penetrate further into the biofilm matrix. As the water, chelating reagents and surfactant penetrate the biofilm it swells, freeing up the interstitial spaces in the matrix lattice and thus allowing further penetration of the reactive agents. As the biofilm matrix swells it reaches a point where a combination of shear forces from the water flow combined with mechanical failure of the biofilm matrix causes agglomerates to slough of the walls and be dispersed into the bulk water. The discoloration of the biofilms during the treatment indicate that the color pigments are being removed or extracted from the biofilm matrix. This mechanism is further supported by the fact that the biofilm isolated in the sump and filter which is in essence a clone of the biofilm on the pipes had significantly fewer microorganisms indicating the ones in the outer layers of the matrix had been destroyed or extracted. Also, the continued presence of low levels of planktonic bacteria in the bulk water, when the lab studies indicate there should be none at these concentrations, infers a slow release of microorganisms over the treatment time, most likely from the breakdown of the biofilm matrix.

After the treatment, the pilot cooling tower system was flushed and the sump cleaned. The system was charged with a fresh water solution (no additional biocide treatment was added) which was circulated throughout the system. Samples were taken at the end of one week and processed for the presence of microorganisms. The plate count results were below the detection limit.

The cooling tower system was fabricated entirely from plastic components so a series of corrosion tests were performed to determine the effect of the process on copper and mild steel. A solution with the same concentration of reagents used in the pilot cooling tower was prepared and placed in corrosion pot test system. The solution was stirred continually for two weeks after which the coupons were removed and analyzed for corrosion. The results showed corrosion rate of mild steel to be between 0.5 and 1.0 mpy, which is below the accepted standard of 3.0 mpy. An industry standard corrosion inhibitor, when run in the same test, gave corrosion rates of 2.0 mpy. The copper coupons showed much higher corrosion rates of 1.2 mpy which is higher than the accepted standard of 0.2 mpy. When the experiment was repeated with 15000 MT, a different corrosion inhibitor commercially available from NCH Corporation or its divisions, added at recommended use concentrations, the copper corrosion rates decreased to 0.3 which is much closer to the acceptable industrial standard. It was determined that the presence of a copper inhibitor (present at a 2 ppm level) was sufficient to reduce copper corrosion and it also shows that the treatment composition does not react with this corrosion inhibitor at these concentrations. This compatibility enables these two products to be used together in a treatment program.

EXAMPLE 3

Treatment of the Pilot Cooling Tower with the Maximum Concentration Reagents and a Secondary Biocide A second study was conducted with a second pilot cooling tower. Unlike the first study in Example 2, this pilot cooling tower had water in the system for 7 months. The internal surfaces of the pipes and tubing were covered in a tar-like black biofilm. The bottom of the sump had a number of deposits and the slide of the sump had a slimy feel indicating the presence of microbial growth. Microbiological analysis of the water in the sump and the biofilm showed $4 \times 10^5$ cfu per ml in the water and $2 \times 10^7$ cfu per cm$^2$ in the biofilm on the sump. In addition, analysis of the microorganism population showed a much greater diversity in species when compared to the microorganisms in Example 2. The pilot cooling tower was treated with the a concentrated solution of the citric acid, sodium citrate, and tetradecyltrimethyl ammonium bromide so that when all the components were added to the water in the system, the reagent concentration was at the maximum level of 0.01M, sodium citrate, 0.005 M citric acid, and 0.0015 M tetradecyltrimethyl ammonium bromide. A secondary biocide, MB2128, was added to give a final concentration of 200 ppm. Samples of the sump water were collected at 24 hours and after 4 days and a swab of the biofilm were collected after 4 days.

Analysis of the sump water showed that the planktonic count in the bulk water was below the detection limit after 24 hours and remained below the detection limit for the remainder of the experiment. It was noted that there was some growth on plates that were plated using 50 μL samples which indicates that there are small agglomerations of biofilm in the bulk water that are protecting the microorganisms as the biofilm sloughs off the surfaces and these are released in the plating process. As with Example 2, the biofilm coloration lightened from black to a very light brown color. Swab samples on the thin areas of the biofilm produced counts that were below the detection limit and swabs taken in areas of biofilm that were thicker resulted in counts of $2 \times 10^2$ cfu per cm$^2$.

Figure 2:
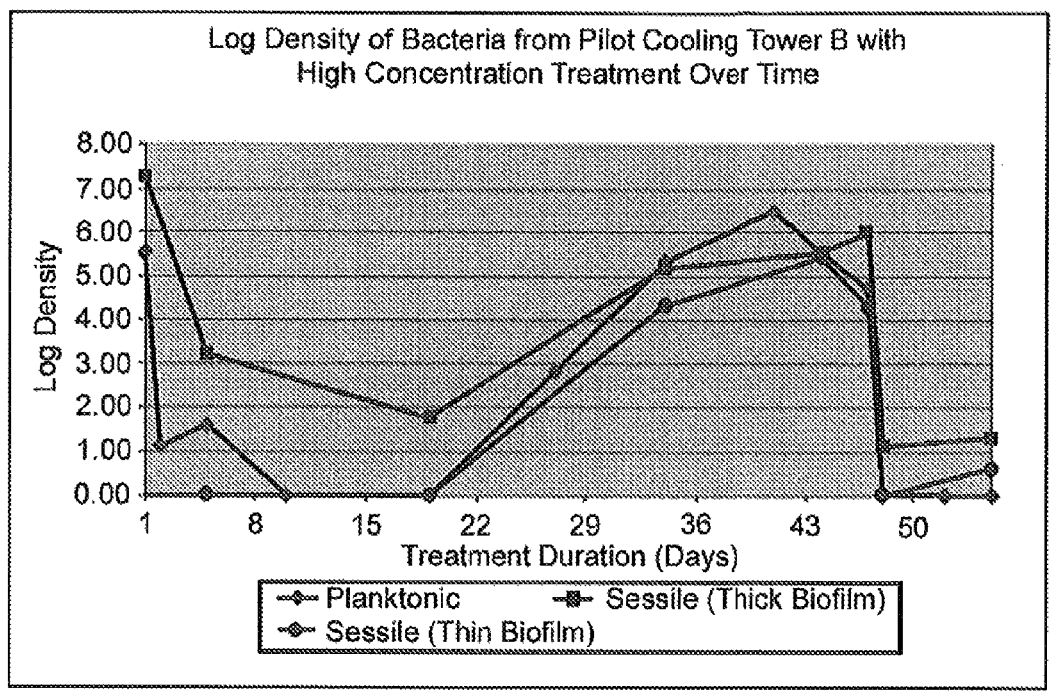
FIG. 2 is a graphical plot of log reduction in planktonic and sessile bacteria resulting from treatment with maximum concentration treatment composition.

Once the experiment was complete the system was drained, and refilled with fresh water that was circulated throughout the system. Unlike Example 2, the solids that were sloughed off during Example 3 remained in the sump and other low flow areas. During this time water loss resulting from evaporation was made up by the addition of fresh water. During the experiment it was noted that there was foam present on the surface of the water in the sump. Microbiological samples were collected on weekly intervals of the sump water and the results of the analysis are shown in FIG. 2. The chart in FIG. 2 shows that for about 20 days after treatment, the microbial population in the system remained under control. However, there was a rapid increase in both sessile and planktonic bacteria over the next 10 days bringing the populations of both up to the normal starting level again. These results indicate that a biofilm is reestablishing itself on the surface of the tubing. Because the pilot cooling tower was not drained and re-filled with fresh water after the treatment cycle was complete, it is believed that the planktonic microorganisms utilized the organic load left over from the treatment composition as a food source, as indicated by the bacterial high counts in the bulk water. Bleeding or draining the system after the treatment cycle was complete, and removing any remaining solids from the sump, would have removed most of this organic load, resulting in the system remaining under control for a longer period of time.

EXAMPLE 3A

Treatment of the Pilot Cooling Tower with the Maximum Concentration Reagents in Powdered Form and a Secondary Biocide At day 48, the cooling tower of Example 3 was treated again, this time with the maximum concentration reagents in powder form. This example demonstrates that there was no difference in performance between the power and liquid treatment compositions. As shown in FIG. 2, within three hours of the addition of the treatment composition in powdered form, both sessile and planktonic bacteria were reduced to levels below the detection limit and they remained at these low levels for over 1 week.

Corrosion evaluations on the maximum concentration for the treatment composition were performed on coupons in the corrosion rack in the cooling tower and in pot tests as previously described. The corrosion coupons in the coupon rack showed signs of corrosion after 24 hours. However, the galvanized steel coupons developed a waxy build up on the surface that increased in thickness with reaction time. The deposit was found to be a combination of the sodium citrate, citric acid, and the surfactant. It also contained zinc, copper and iron. This deposit was only observed on the zinc coupon in the coupon rack. Other zinc coupons that were placed in the sump, which is a low flow environment, did not show any sign of this waxy build up. The results from the corrosion pot tests showed that without the addition of the 15000 MT corrosion inhibitor, the corrosion rates were 30 mpy for mild steel and 4 mpy for copper. It was also noted that a waxy deposit formed on both the copper and mild steel coupons which had the same spectrum as that found on the zinc coupon in the tower. Corrosion rates with the addition of 15000 MT were unchanged for mild steel, however; copper corrosion rates were decreased by an order of magnitude to 0.4 when the 15000 MT corrosion inhibitor was used.

The results from these Examples help define how this treatment composition can be applied to treat real anthropogenic water system based on overall performance and reactivity. The treatment composition works by reacting with the biofilm in a synergistic chemical and physical interaction that causes it to slough or exfoliate from the surface it is attached to. As it breaks from the surface it forms small agglomerates that contain viable microorganisms. Failure to remove the biofilm agglomerates dislodged as a result of the treatment can lead to rapid re-colonization of the system. The minimum concentration treatment requires several days to act; however; corrosion rates are low especially when used with a corrosion inhibitor. The higher concentration treatment requires a shorter exposure time up to 24 hours, however, it is highly corrosive to the metals in the system. The higher concentration treatment has the potential to form a thick waxy build up in galvanized surfaces in areas where there is high laminar flow. The addition of corrosion inhibitors is preferred, especially for water systems that contain copper. Adding the reagents in powder form significantly reduces the volume of material required for the treatment without negatively impacting the efficacy of the treatment.

EXAMPLE 4

Treatment of a 600 Gallon Cooling Tower

This
Example was designed to apply the laboratory results to a small scale cooling tower in the field. This example was carried out on a CTS model 2125, 125 ton cooling tower with a total volume of 600 gallons located on the campus of a local University. The cooling tower was used to cool the computer building and was operating with a full heat load for the duration of the test.

Prior to performing the test the cooling tower was being treated using a conventional biocide protocol. The conventional biocide treatment was stopped two weeks prior to the treatment using the treatment composition and method of the invention. Water samples were collected and analyzed prior to the treatment to give base line readings. The condition of the system was also documented photographically. It was noted that the water in the system was clear; however, a thin film of algae was growing on the bottom of the sump. There were no signs of other deposits in the sump. The fill material had a black film formed throughout the entire structure. The film was a mixture of biological and inorganic compounds. Swab testing showed a microbiological load of $2 \times 10^6$ cfu per cm$^2$. Analysis of the sump gave an initial count of $1 \times 10^2$ cfu per ml with the majority of the microorganisms identified as *pseudomonas* spp. Dissolved and suspended copper were within acceptable ranges as was the dissolved and suspended iron.

Prior to initiating the treatment, the cooling tower system was flushed, fresh water added, then the bleed valve was disconnected from the conductivity controller. For protection of the copper in the chiller system, a tolyltriazole (TTA) compound was added to give a total of 9 ppm in the bulk water and this was circulated through the system for 1 hour. A treatment composition comprising citric acid, sodium citrate, tetradecyltrimethyl ammonium bromide solids (in powdered form) were weighed out in amounts that when added to the water in the cooling tower would give a final concentration of 0.005 M sodium citrate, 0.003 M citric acid, and 0.00075 M tetradecyltrimethyl ammonium bromide. The powders for each component were added to a drum and mixed together to generate a uniform blend. Water from the sump was mixed with the solids in the drum and the resulting slurry was introduced directly into the sump of the cooling tower. Secondary biocide, MB2128, was added directly to the sump at the recommended use levels. An in line filter was placed over the exit pipe from the cooling tower to the condenser during the treatment cycle to filter out solids dislodged by the treatment.

Once the compound was added a thin layer of foam formed where the water falling from the fill hit the water in the sump. As the product circulated it was noted that the water changed from colorless to semi-transparent grey and it was no longer possible to see the bottom of the sump. The product circulated for 48 hours, then the cooling tower system was dumped and fresh water was added and the conventional biocide program reinstated.

Figure 3:
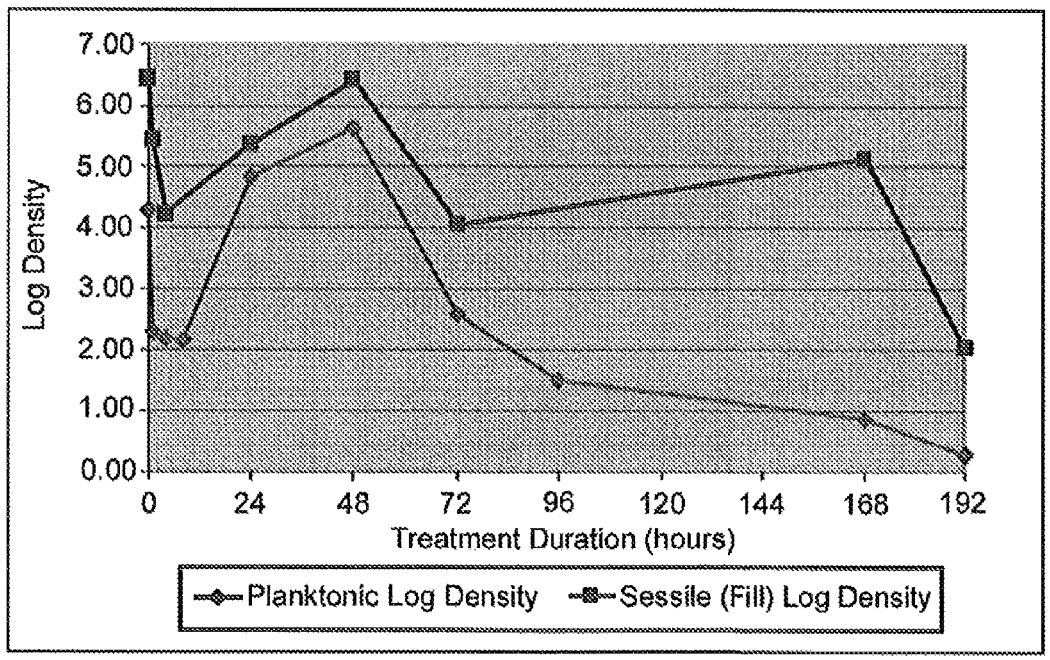
FIG. 3 is a graphical plot of planktonic and sessile bacteria isolated from the cooling tower as a function of time.

FIG. 3 is a graph of the planktonic and sessile bacteria isolated from the sump and fill during the experiment of Example 4. The graph shows that immediately after the addition of the treatment composition there was a drop in the viable bacteria load in both planktonic and sessile forms. However, it was observed that at 24 hours (for the planktonic bacteria) and 48 hours (for the sessile bacteria), the number of viable bacterial had increased to the almost the original values. The microbiological analysis showed that in the initial measurements the colonies looked like normal *pseudomonas* spp. but after 24 hours a second species originally thought to be contamination began to appear on the plates. When these species were identified they were found to be a *pseudomonas* spp that was different from the first ones observed. Additional analysis showed that there were protozoa species present in the water that were not present in the initial analysis. With the addition of the conventional biocide after the treatment there was a significant drop in the number of viable planktonic and sessile bacteria in the cooling tower system.

During the treatment in Example 4, it was observed that the black biofilm on the fill material was loosened and began to fall off into the sump. A spray of water taken from the sump was used to remove the remaining material from the fill material.

A green/grey deposit was observed on the filter. Analysis of the deposit material showed it to have the following composition: Organic 37%, Calcium Carbonate 18.5%, Silica 31% with the remaining being zinc, aluminum and iron oxides.

As observed with the other Examples, the treatment discolors the biofilm, swelling it and causing it to slough off in agglomerates and to delaminate from the surfaces of the water system. The results also show these agglomerates contain viable bacteria and that these bacteria can re-colonize the system, even when an in-line filter is in place to remove the solids. However, the results show that addition of another secondary biocide after the bio-dispersion treatment (in addition to the amount of MB2128 that was added to the sump at the beginning of the treatment) is effective at reducing the viable microorganisms in the planktonic and sessile state.

Figure 4:
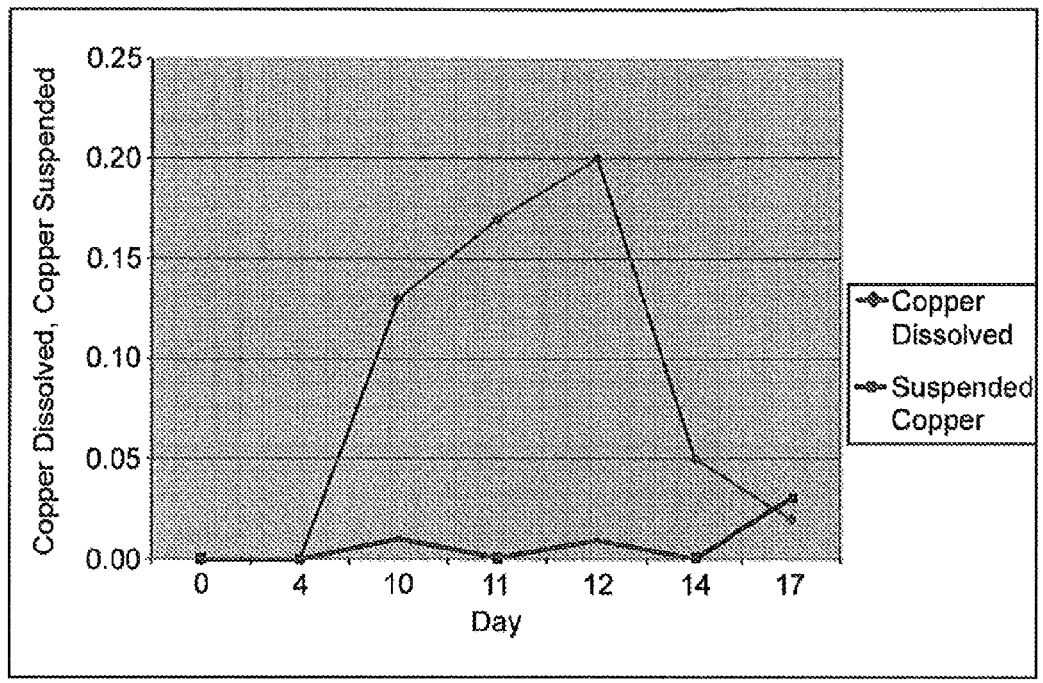
FIG. 4 is a graphical plot showing dissolved and suspended copper in the bulk water as a function of time.

FIG. 4 is a graph showing copper dissolved and suspended in the bulk water of the cooling tower before, during, and after the treatment. The graph shows that prior to the treatment, the copper levels in the system were essentially zero. On the day the test was started the copper levels began to climb and they remained high even after the 48 hour treatment cycle was completed and the water containing the dissolved treatment composition was flushed from the system. However, the values returned to the normal low levels after several days of normal operation. These results indicate, as observed in the prior Example, in that long term exposure (such as a treatment cycle of 48 hours or longer) of cooper to the treatment composition could be detrimental to the water system performance and/or copper components of the water system. As such, it is most preferred to use a copper corrosion inhibitor with the treatment composition to prevent excessive corrosion.

An additional benefit of the treatment according to this embodiment of the invention is that it seemed to be effective at removing or discoloring algae from the sides of the sump. The results from the field experiment in Example 4 showed that when used in a controlled manner and following the procedures outlined above this treatment composition is effective at removing biofilm, scale, and algae.

EXAMPLE 5

Treatment of a 700 Gallon Cooling Tower

Another experiment was conducted on a cooling tower that was considered to be a clean tower. A Marley 700 gallon cooling tower was identified and inspected for signs of visible contamination. It was noted that the water was clear, there was some brown deposits on the fill in the water, and there was a small amount of calcium carbonate scale on the outer surfaces of the fill. One week prior to starting the experiment, the conventional biocide treatment program was stopped. Microbial analysis of the water and brown deposit on the fill prior to starting the experiment showed counts of $1 \times 10^4$ cfu per ml and $1 \times 10^4$ cfu per cm, respectively, which are well within the specifications for this tower to be considered clean.

The treatment composition concentration was the same as that used in the previous experiments with the only change being the surfactant, which was switched to didecyldimethyl ammonium chloride. Prior to treatment a 17 ppm tolyltriazole solution, a copper corrosion inhibitor, was added to the sump and was allowed to circulate for 1 hour. After the hour had elapsed, the surfactant was added directly to the sump of the cooling tower and it was allowed to circulate for 24 hours. After 24 hours the other reagents were added.

It was observed that with the initial addition of the surfactant the water turned turbid but within 24 hours it had turned clear again. There were no signs of deposits or other material present in the water. With the addition of the other reagents the liquid began to turn green around the edges of the sump where the fill was located.

After 4 hours of treatment the system was set to bleed and the tower was filled with fresh water. The next day when the tower was inspected it was found that there was a significant amount of foam built up inside the tower. The foam had a considerable amount of green material over the surface. Most notably in the bottom of the sump was a light green deposit that was not there the previous day. Although the deposit looked like it was a copper oxide or a copper compound, it was determined to contain 92% organic material with the remainder being zinc oxide and calcium carbonate upon analysis. This indicated that the cooling tower contained more organic material than initially appeared by visual inspection and the water analysis and that the treatment was effective at removing organic material from the surfaces of the tower Because of the time of the year and the low heat load on the system the water did not cycle as quickly as expected so even after the blown down process there was still citrate and surfactant in the system. This became problematic as the continued action of the reagents released more organic material into the sump of the cooling tower, which may then re-contaminate the system. Irregular flow patterns through the system lead to excessive foaming which required treatment with antifoam.

Figure 5:
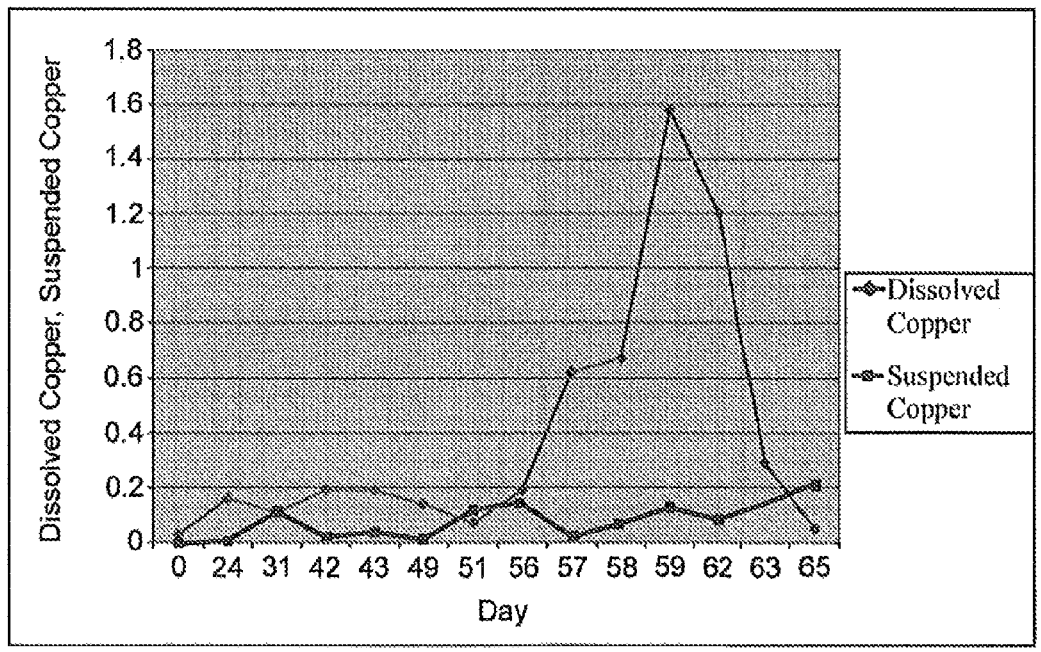
FIG. 5 is a graph showing dissolved and suspended copper as a function of time.

Additionally, the presence of the citrate and surfactant reagents in the system even after the system was bled, resulted in further corrosion of the copper elements of the system. FIG. 5 is a graph showing the dissolved and suspended copper in the cooling tower system. Even after the cooling tower system had been flushed, there was a continued dissolution of the copper in the system and that rate of corrosion is excessive. In order to prevent permanent damage to the cooling tower system the entire unit was bled, and power washed before being filled up with fresh water. Analysis showed that after this process the copper levels returned to normal. Accordingly, it may be necessary to rinse or clean the water system after bleeding or draining the water system upon completion of the treatment cycle to fully remove the reagents prior to filling the system with fresh water.

Figure 6:
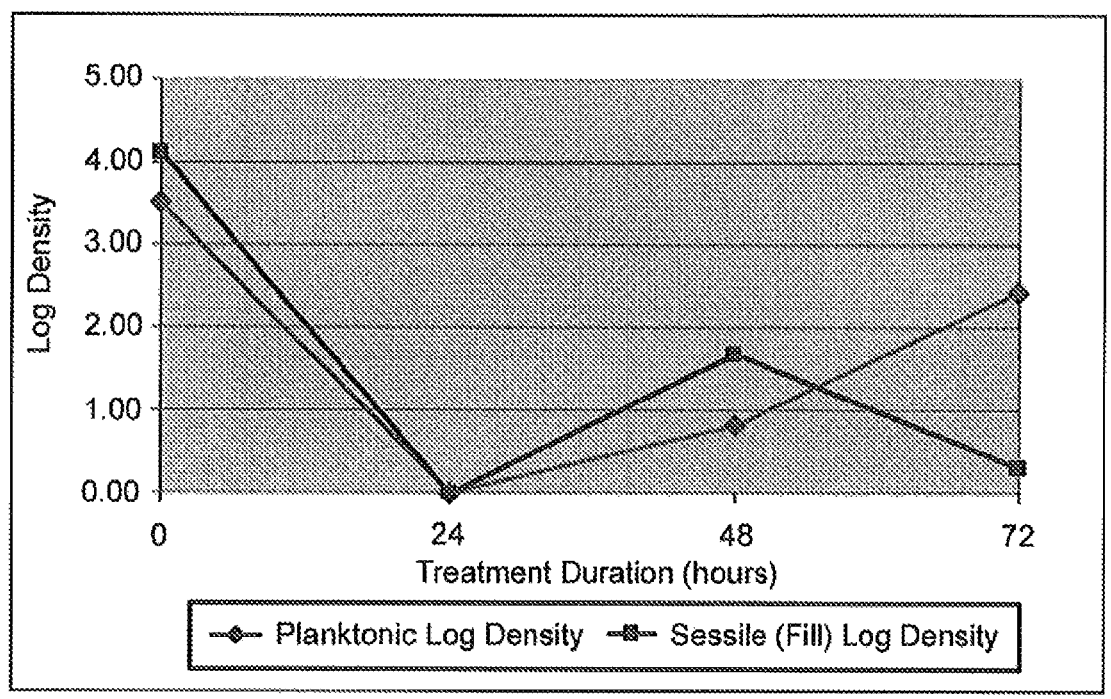
FIG. 6 is a graph showing the planktonic and sessile bacterial counts in Example 5.

FIG. 6 is a graph showing the planktonic and sessile counts from the tower in Example 5. As expected, there is an initial decrease in the planktonic and sessile counts; however, as more of the biofilm material is released into the sump and the concentration of treatment composition is decreased as the reagents are consumed and with the initial bleed, the number of viable microorganisms began to increase again.

EXAMPLE 6

Treatment of a 3,500 Gallon Cooling Tower

In another study, a cooling tower with a volume of 3,500 gallons was treated with a composition according to the invention. The treatment was prepared with the neutral salt and organic acid being mixed together in small containers (1-5 gallon capacity) and the surfactant being pre-prepared in a separate container. Prior to adding the treatment composition, 265 g of the tolytriazole was added to the water system, followed by 795 g of an antifoaming agent. The treatment composition was then added to the sump by adding 3.5 gallons of the neutral salt/organic acid mixture, followed by 3.5 gallons of the surfactant. The solution was allowed to mix and the final concentration of the reagents in the water was 0.005 M sodium citrate, 0.003 M citric acid, and 0.00075 M didecyldimethyl ammonium chloride.

After addition of both parts of the treatment composition, a thin layer of foam started to form in the sump. The highest level of foam was in proximity to the make-up valve which was the area of the most turbulence. Also, a thin layer of foam formed where the water falling from the fill splashed into the water level in the sump. As the reagents circulated through the system, the water became slightly hazy and the bottom of the sump was not as visible. The water also turned turbid at the pour point of the surfactant addition, but it cleared up during the treatment cycle.

Dissolved and suspended copper were monitored before and during the treatment cycle. The dissolved copper level climbed up to about 0.2 ppm during treatment and quickly dropped once the bleed valve had been opened. Suspended copper level remained about the same during treatment cycle. Because the treatment composition is corrosive to copper, the addition of a copper corrosion inhibitor, such as tolyltriazole is preferred.

An ATP analysis, based on the detection of Adenosine Tri-Phosphate which is present in living (viable) cells, was used in this Example to determine the biological load in the water system. The detection of ATP indicates the water system contains living cells. An ATP analysis may also detect non-cell bound ATP released in the bulk water, but such non-cell bound ATP has a very short life-time and quickly degrades outside of the cell. When biofilms are present within a water system there is typically a rapid rise in the total ATP following biodispersant addition. The rise in total ATP is due to biodispersant transferring cells from the surfaces of the water system into the bulk water. Once biocide is added to the system, it kills circulating biofilm as well as newly-exposed layers of the biofilm adhered to the surfaces of the system and a convergence of total ATP can be detected. In this Example, the total ATP was tested before, during and after the treatment cycle. Total ATP went up to 4200 RLU when the treatment composition was added into the system, suggesting circulating biofilm in the bulk water. Once MB-60B (a secondary biocide) was added to the system, the total ATP quickly dropped back to its initial values as measured prior to addition of the treatment composition.

The results of the field trials are summarized as follows: (1) The treatment composition and method are best used in cooling towers or water systems where there is a high water exchange due to heavy heat loads; (2) the treatment composition will attack copper present in the water system being treated (such a copper tubing in the chiller units of a cooling tower), so the use of a corrosion inhibitor is preferred; (3) the treatment composition is effective at removing organic, biological and inorganic materials that have built up on the surfaces of the water system; (4) once the treatment cycle is complete, returning to a conventional biocide treatment is an effective way to keep the microbial populations under control, but repeated, periodic treatments with the treatment composition and method of the invention are preferred; (5) the use of the reagents in the treatment composition in powdered form is effective; (6) the reagents in the treatment composition can be added directly into the sump or other water reservoir and diluted with the water already in the anthropogenic system being treated; (7) the treatment will release agglomerates into the system that contain microorganisms that are normally not present in the bulk water system; and (8) the biofilm agglomerate can be effectively removed from the system with the use of an inline filter.

EXAMPLE 7

Treatment of *Legionella* Biofilms

A *Legionella pneumophila* (ATCC 33153) biofilm was grown in the CDC reactor under 4 days of continuous buffered charcoal yeast extract media supply. A rod with three stainless steel coupons was then sampled for viable cell counts prior to treatment exposure. Additional rods were transferred to batch reactors containing either buffered dilution water (control coupons), minimum concentration reagents or high concentration reagents of the treatment composition according to the invention. After 1 hour and 24 hours, a rod was pulled from each reactor and sampled for viable cell numbers. There was a 1.4 and a 2.4 log reduction in *legionella* in a biofilm for the minimum and maximum treatment concentrations, respectively.

EXAMPLE 8

Foaming Treatment of a Dialysis Drain at Maximum Concentration

Another study was conducted using a foaming treatment on a dialysis drain at a local hospital. A solution with a concentration of active reagents comprising 0.01 M sodium citrate, 0.005 M citric acid, and 0.0015 M Neodol 91-6 as the surfactant was prepared using deionized water. A 300 ml aliquot of the solution was transferred into an aerosol can in combination with Neodol 91-6 (in addition to the Neodol 91-6 used as the surfactant component of the treatment composition, which was added to improve the foaming properties), sodium benzoate (a preservative as a corrosion inhibitor), AMP-95 (an extra foamer), and 20 g of AB-46 (a propellant). The aerosol can was fitted with a foaming nozzle and stem, sealed, and then pressurized. The can should be fitted with a nozzle that will best deliver the treatment composition to substantially all surfaces in the drain, which will depend on the structure and physical configuration of the drain being treated. Any compatible surfactant may be used, although Neodol 91-6 is preferred. A high foaming surfactant is best for the aerosol application in order to extend contact time as long as possible.

Upon arriving at the treatment site, the tube connecting the dialysis machine and the drain was removed and placed in a biohazard bag. The drain cover was removed and the drain was inspected visually and photographically for the presence of deposits and biofilm. The inspection revealed the presence of a dried waxy build up and biological growth on the sides of the drain leading to the main drain line. Microbiological samples inside the drain at the water-air interface were taken before and after treatment.

The treatment composition was applied to the drain as a foam from the aerosol can, in a manner that completely filled the drain line from the water level to the top of the drain line. As the foam broke, additional treatment composition was applied to maintain the foam column height. The foam remained in the drain line for 1 hour after which it was washed away using a hand held sprayer charged only with tap water. It was noted that at the end of the treatment, biological debris were present in the foam and when it was rinsed with water, the sides of the drain walls looked visibly cleaner. It was also noted that the foul odor emanating from the drain was considerably less at the end of the treatment. Once the foaming treatment was complete, the system was treated with a regular maintenance dose of a conventional, commercially available drain treatment product.

EXAMPLE 9

Foaming Treatment of a Dialysis Drain at Minimum Concentration

A second study on the dialysis drain was conducted using a treatment composition having to the minimum concentrations of 0.001 M Sodium Citrate, 0.0005 M Citric Acid, and 0.00015 M surfactant. The treatment composition was applied to the drain as a foam in a manner that completely filled the drain line from the water level to the top of the drain. There was no difference in the consistency of the foam when compared to Example 8. As the foam broke, additional treatment composition was applied to maintain the foam column height. The foam remained in the drain line for 1 hour before being flushed from the line with tap water, then treated with a conventional, commercially available drain maintenance chemical program. As with Example 8, the sides of the wall of the drain line looked cleaner and there was a reduction in the bad odor coming from the drain line.

EXAMPLE 9A

Liquid Treatment of a Dialysis Drain at Minimum Concentration

A third study was conducted to compare a liquid treatment composition to the foaming composition of Example 9. A solution of the treatment composition without the additional aerosol agents was prepared to give an active concentration of 0.001 M Sodium Citrate, 0.0005 M Citric Acid, and 0.00015 M surfactant. The drain line was opened and an inflatable drain plug was inserted to reach the bottom of the drain line. The plug was connected to an air pump and inflated to 40 psi causing it to seal the drain. The liquid treatment composition was poured down the drain and left to react for 1 hour. After the treatment time had elapsed, the plug was deflated and the liquid was allowed to run down into waste. The walls of the drain line were washed with tap water and a conventional, commercially available drain maintenance product [was then added. In addition to the visible reduction on contaminants within the drain after the treatment, swab analysis showed that there was a reduction of microorganisms on the drain line wall after the treatment.

The results of the experiments show that both the liquid and foam applications are effective at cleaning biological material from the walls of the drain lines. However, the experimental observations showed that the foam exposed the surface to fresh active chemical through the action of the foam breaking and also seemed to help physically remove the biological soil from the surface of the drain line.

Table 3 shows the results of microbiological analysis of swab samples collected from the sides of the drain walls in Examples 8 and 9. Two swabs, labeled A and B, were taken for each drain and for each application of the foaming treatment composition, at the maximum concentration and the minimum concentration. A treatment composition according to one embodiment of the invention was applied, followed by an application of commercially available Drain Tain, then the swabs were taken at different locations on substantially opposites sides of the drain. These results showed that the microorganism count was reduced by an average of 5 logs for both treatment compositions.

TABLE 3

Microorganisms from Drain Walls

| Drain No. | Treatment | Sample | Before Treatment CFU/mL | After Treatment CFU/mL |
|---|---|---|---|---|
| 1 | Drain-Tain (Prior-Art Treatment/Control) | Swab 1A | $2.00 \times 10^1$ | $5.00 \times 10^0$ (Below limit of quantitation) |
| 1 | Drain-Tain (Prior-Art Treatment/Control) | Swab 1B | $9.75 \times 10^7$ | $1.00 \times 10^1$ Below limit of quantitation |
| 2 | Example 9 (Min. Conc.), followed by Drain-Tain | Swab 2A | $1.88 \times 10^7$ | Below limit of detection |
| 2 | Example 9 (Min. Conc.), followed by Drain-Tain | Swab 2B | $2.20 \times 10^2$ | $1.18 \times 10^1$ (Below limit of quantitation) |
| 3 | Example 9 (Min. Conc.), followed by Drain-Tain | Swab 3A | $4.20 \times 10^5$ | $1.5 \times 10^2$ (Below limit of quantitation) |
| 3 | Example 9 (Min. Conc.), followed by Drain-Tain | Swab 3B | $2.71 \times 10^3$ | Below limit of detection |
| 4 | Example 8 (Max. Conc.), followed by Drain-Tain | Swab 4A | $5.65 \times 10^8$ | $1.29 \times 10^3$ |
| 4 | Example 8 (Max. Conc.), followed by Drain-Tain | Swab 4B | $7.50 \times 10^8$ | $9.85 \times 10^4$ |
| 5 | Example 8 (Max. Conc.), followed by Drain-Tain | Swab 5A | $2.50 \times 10^1$ (Below limit of quantitation) | $1.05 \times 10^2$ (Below limit of quantitation) |
| 5 | Example 8 (Max. Conc.), followed by Drain-Tain | Swab 5B | $1.30 \times 10^1$ (Below limit of quantitation) | $2.00 \times 10^1$ (Below limit of quantitation |

EXAMPLE 10

Treatment of Waterless Urinals

Another study was conducted using the foaming treatment composition to remove and prevent the reoccurrence of biological build up in waterless urinal systems. Prior to adding the treatment composition, the drain plug leading from the urinal to the drain was removed revealing a layer of biological and inorganic deposits at the air-liquid interface. The drain line was filled with the foaming product delivered from an aerosol can with a concentration of active ingredients 0.01 M sodium citrate, 0.005 M citric Acid, and 0.0015 M didecyldimethyl ammonium chloride. The treatment was allowed to react for 5 minutes after which the foam was rinsed with water and a conventional sealer was added. The control urinals had the drain line brushed and conventional sealer added. The first week after treatment there were no visible changes in the condition of the sealer or odor control blocks. The second week, the untreated urinals started to show signs that the odor control systems were breaking down. The urinals to which the foaming treatment composition was applied had fully functional odor control systems and were odor free. After week three, some of the odor control blocks in the untreated urinals started to exhibit biological growth and the sealer was changing color from blue to green, whereas the treated urinals showed little to no biological build up. After 4 weeks the odor control systems in the untreated urinals had broken down completely, while the treated urinals were still fully operational and exhibited controlled odors.

In additional to the previous results, the results of these drain and urinal examples are summarized as follows: (1) the foaming treatment composition is preferred for use in cleaning drain systems because it is easier to apply to substantially all contaminated surfaces in drain systems and the physical breaking of the foam helps mechanically remove biological based material from the walls of the drain system; (3) the treatment composition helps eliminate foul odors in drain systems; (4) the treatment composition may extend the lifetime of a clean, unclogged drain, especially in the case of the waterless urinals; (5) the treatment composition is preferably allowed to contact the surfaces of a drain system for 5-120 minutes, but a contact time of around 60 minutes is most preferred; (6) the treatment composition eliminates or minimizes food sources/harborages for invertebrate insects within drain systems; (7) the residual effects of the treatment help prevent biofilm from growing back in drain systems.

The concentration ranges for neutral salt, acid salt, and surfactant reagents provided herein are based on the quantities of these reagents in the total volume of water in the water system being treated, prior to the addition of any other additives, such as corrosion inhibitors, anti-foaming agents, or any secondary biocide. Such additives may be incorporated into a pre-mixed composition with the neutral salt, acid salt, and surfactant according to an embodiment of the invention and those of ordinary skill in the art will understand and appreciate the corresponding change in concentrations when the additional ingredients are included. References herein to water systems that are not capable of holding a volume of water include systems that are actually capable of holding a volume of water, either as they currently exist or through modification, but for which it is desired for any reason to apply the treatment composition of the invention without plugging the system or otherwise using an shut-off mechanism to hold a volume of water within the system. Additionally, the use of the terms flowing (or circulating) and non-flowing (or non-circulating) to describe water systems is not intended to limit the scope of the invention, as the embodiments of the composition, method, and system may be used with either type of system with modifications described herein or that will be understood by those of ordinary skill in the art. Those of ordinary skill in the art will also appreciate upon reading this specification, including the examples contained herein, that modifications and alterations to the composition and methodology and system for using the composition may be made within the scope of the invention and it is intended that the scope of the invention disclosed herein be limited only by the broadest interpretation of the appended claims to which the inventor is legally entitled.

We claim:

1. A method of removing biofilm in a water system, the method comprising the steps of:
   removing water from the water system;
   adding a volume of fresh water to the water system;
   adding a treatment composition to the water in the water system after the removing step, the treatment composition comprising a first chelating agent in a concentration in the range of about 0.0005 M to 0.005 M, a second chelating agent in a concentration in the range of about 0.001 M to 0.01 M, and a cationic surfactant in a concentration in the range of about 0.00015 M to 0.0015 M, wherein the concentrations are of these ingredients when mixed with the volume of water in the water system being treated;
   contacting the water containing the treatment composition with components of the water system for a first period of time to remove biofilm attached to surfaces of the components of the water system; and
   adding a first amount of biocide to the water in the water system after the treatment composition addition step.

2. The method of claim 1 further comprising the steps of:
   adding a corrosion inhibitor to the water in the water system prior to adding the treatment composition to the water; and
   contacting the water containing the corrosion inhibitor with components of the water system.

3. The method of claim 1 wherein the water containing the treatment composition contacts the components of the water system by circulating through the water system.

4. The method according to claim 1 wherein the first chelating agent is an organic acid and the second chelating agent is the corresponding neutral salt of the first chelating agent.

5. The according to claim 1 wherein the chelating agents and surfactant are in solid form the water of the water system being treated.

6. The method of claim 1 further comprising the step of disabling any automatic bleeding mechanism in the water system that triggers bleeding based on conductivity levels of the water to prevent bleeding during the first period of time and wherein the first period of time is 24 to 48 hours.

7. The method of claim 2 further comprising the steps of removing substantially all of the water from the water system after adding the first amount of biocide to the water in the water system;
   adding fresh water to the water system; and
   adding a second amount of biocide to the water system.

8. The method of claim 2 wherein the water system is a circulating water system and the water containing the corrosion inhibitor contacts the components of the water system by circulating through the water system.

9. The method of claim 2 further comprising the step of monitoring the water system for corrosion during the time the treatment composition contacts components of the water system.

10. The method of claim 2 further comprising the step of disabling any automatic bleeding mechanism in the water system that triggers bleeding based on conductivity levels of the water to prevent bleeding during the first period of time and wherein the first period of time is 24 to 48 hours.

11. The method according to claim 2 wherein the first chelating agent is citric acid and the second chelating agent is sodium citrate.

12. The method of claim 3 further comprising the step of:
   filtering the water as it circulates through the water system to remove agglomerates of biofilm that have detached from surfaces of the components in the water system.

13. The method of claim 3 wherein the surfactant is added to the water in the water system and allowed to circulate prior to adding the chelating agents.

14. The method according to claim 4 wherein the first chelating agent is citric acid and the second chelating agent is sodium citrate.

15. The method according to claim 4 wherein the surfactant is an ammonium bromide or ammonium chloride compound.

16. The method of claim 6 further comprising the steps of:
- removing substantially all of the water from the water system after adding the first amount of biocide to the water in the water system;
- adding fresh water to the water system and
- adding a second amount of biocide to the water system to reduce bacteria remaining in the water system after treatment with the treatment composition.

17. The method according to claim 6 wherein the first chelating agent is citric, acid and the second chelating agent is sodium citrate.

18. The method of claim 10 wherein the corrosion inhibitor is added to the water system for 1 hour.

19. The method of claim 16 further comprising the steps of:
- adding a corrosion inhibitor to the water in the water system prior to adding the treatment composition; and
- contacting the water containing the corrosion inhibitor with components of the water system.

20. A method for treating a water system to remove a biofilm, the method comprising:
- contacting a corrosion inhibitor with components of the water system for a first period of time;
- contacting a treatment composition having concentrations of at least 0.0005 M organic acid, 0.001 M neutral salt of the organic acid, and 0.00015 M surfactant with components of the water system for a second period of time; and
- flushing water from the water system after the second period of time to substantially remove any remaining treatment composition and corrosion inhibitor;
- wherein the concentrations are of these ingredients when mixed with the volume of water in the water system being treated;
- wherein the first period of time is prior to the second period of time; and
- wherein the second period of time is effective to remove biofilm attached to surfaces of the components.

21. The method of claim 20 wherein the the corrosion inhibitor has a concentration around 2 ppm to 20 ppm when mixed with the volume of water in the water system being treated.

22. The method of claim 20 wherein the neutral salt is sodium citrate, the acid is citric acid, and the surfactant is an ammonium bromide or ammonium chloride compound.

23. The method of claim 20 wherein the neutral salt is sodium citrate, the acid is citric acid, and the surfactant is an alcohol ethoxylate or an alcohol ethoxysulfate compound.

24. The method of claim 20 where the water system is a drain and the treatment composition removes substantially invertebrate insect food sources within the drain.

25. The method of claim 20 further comprising the step of disabling any automatic bleeding mechanism in the water system that triggers bleeding based on conductivity levels of the water to prevent bleeding during the second period of time and wherein the second period of time is 24 to 48 hours.

26. The method of claim 20 wherein the first period of time is around an hour or longer.

27. The method of claim 20 further comprising the step of adding a first amount of biocide to the water in the water system after the second period of time begins and prior to the flushing step.

28. The method of claim 21 wherein the treatment composition contacts the components of the water system by circulating through the water system.

29. The method of claim 21 wherein the treatment composition is aerosolized or made into a foaming formulation prior to contacting the components of the water system.

30. The method of claim 24 wherein the treatment composition removes substantially all biofilms that contribute to foul odors.

31. The method according to claim 25 wherein the first chelating agent is citric acid and the second chelating agent is sodium citrate.

32. The method according to claim 27 further comprising the step of adding a second amount of biocide to the water in the water system after the flushing step.

33. The method according to claim 32 further comprising the step of disabling any automatic bleeding mechanism in the water system that triggers bleeding based on conductivity levels of the water to prevent bleeding during the second period of time and wherein the second period of time is 24 to 48 hours.

* * * * *